(12) United States Patent
Bold et al.

(10) Patent No.: US 7,390,805 B2
(45) Date of Patent: *Jun. 24, 2008

(54) 4-AMINO-6-PHENYL-PYRROLO[2,3-D]PYRIMIDINE DERIVATIVES

(75) Inventors: Guido Bold, Gipf-Oberfrick (CH); Hans-Georg Capraro, Rheinfelden (CH); Giorgio Caravatti, Bottmingen (CH); Peter Traxler, Schoenenbuch (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/686,023

(22) Filed: Mar. 14, 2007

(65) Prior Publication Data

US 2007/0161632 A1    Jul. 12, 2007

Related U.S. Application Data

(63) Continuation of application No. 10/485,747, filed as application No. PCT/EP02/08780 on Aug. 6, 2002.

(30) Foreign Application Priority Data

Aug. 7, 2001 (GB) ................... 0119249.1

(51) Int. Cl.
 C07D 413/10 (2006.01)
 C07D 487/04 (2006.01)
 A61K 31/519 (2006.01)
 A61K 31/5377 (2006.01)
 A61K 31/497 (2006.01)
 A06P 35/04 (2006.01)

(52) U.S. Cl. ............. 514/234.2; 544/117; 544/280; 514/265.1; 514/252.16

(58) Field of Classification Search ............. None
See application file for complete search history.

(56) References Cited

U.S. PATENT DOCUMENTS

| 5,686,457 | A | 11/1997 | Traxler et al. |
| 5,877,178 | A | 3/1999 | Gangjee |
| 5,958,930 | A | 9/1999 | Gangjee |
| 6,096,749 | A | 8/2000 | Traxler et al. |
| 6,140,332 | A | 10/2000 | Traxler et al. |
| 6,180,636 | B1 | 1/2001 | Traxler et al. |
| 2004/0053908 | A1 | 3/2004 | Funahashi et al. |

FOREIGN PATENT DOCUMENTS

| EP | 0 795 556 | 9/1997 |
| EP | 1 040 831 | 10/2000 |
| WO | 95/33750 | 12/1995 |
| WO | 97/02266 | 1/1997 |
| WO | 97/47601 | 12/1997 |
| WO | 98/06703 | 2/1998 |
| WO | 98/07726 | 2/1998 |
| WO | 98/43973 | 10/1998 |
| WO | 99/65908 | 12/1999 |
| WO | 99/65909 | 12/1999 |
| WO | 01/23389 | 4/2001 |
| WO | 01/47507 | 7/2001 |
| WO | 01/49688 | 7/2001 |
| WO | 01/53263 | 7/2001 |

OTHER PUBLICATIONS

Caravatti et al., "Pyrrolo[2,3-d]pyrimidine and Pyrazolo[3,4-d]pyrimidine Derivatives as Selective Inhibitors of the EGF Receptor Tyrosine Kinase," ACS Symposium series, 796, pp. 231-244 (2001).

*Primary Examiner*—Brenda L. Coleman
*Assistant Examiner*—Susanna Moore
(74) *Attorney, Agent, or Firm*—Oona A. Manzari

(57) ABSTRACT

The invention relates to 7H-pyrrolo[2,3-d]pyrimidine derivatives of formula I

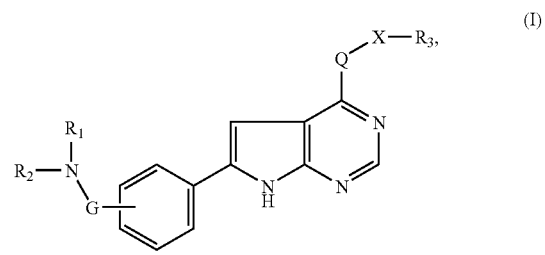

wherein the symbols and substituents are as defined in the description, to processes for the preparation thereof, to pharmaceutical compositions comprising such derivatives and to the use of such derivatives—alone or in combination with one or more other pharmaceutically active compounds—for the preparation of pharmaceutical compositions for the treatment especially of a proliferative disease, such as a tumour.

3 Claims, No Drawings

4-AMINO-6-PHENYL-PYRROLO[2,3-D]PYRIMIDINE DERIVATIVES

This application is a continuation of U.S. application Ser. No. 10/485,747, filed Feb. 3, 2004, which is a 371 of International Application No. PCT/EP02/08780, filed Jun. 8, 2002.

The invention relates to 7H-pyrrolo[2,3-d]pyrimidine derivatives and to processes for the preparation thereof, to pharmaceutical compositions comprising such derivatives and to the use of such derivatives—alone or in combination with one or more other pharmaceutically active compounds—for the preparation of pharmaceutical compositions for the treatment especially of a proliferative disease, such as a tumour.

The invention relates to 7H-pyrrolo[2,3-d]pyrimidine derivatives of formula I

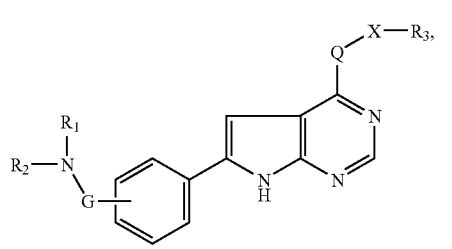

wherein $R_1$ and $R_2$ are each independently of the other hydrogen, unsubstituted or substituted alkyl or cycloalkyl, a heterocyclic radical bonded via a ring carbon atom, or a radical of the formula $R_4$—Y—(C=Z)— wherein $R_4$ is unsubstituted, mono- or disubstituted amino or a heterocyclic radical, Y is either not present or lower alkyl and Z is oxygen, sulfur or imino, with the proviso that $R_1$ and $R_2$ are not both hydrogen; or $R_1$ and $R_2$ together with the nitrogen atom to which they are attached form a heterocyclic radical;

$R_3$ is a heterocyclic radical or an unsubstituted or substituted aromatic radical;

G is $C_1$-$C_7$-alkylene, —C(=O)—, or $C_1$-$C_6$-alkylene-C(=O)— wherein the carbonyl group is attached to the $NR_1R_2$ moiety;

Q is —NH— or —O—, with the proviso that Q is —O— if G is —C(=O)— or $C_1$-$C_6$-alkylene-C(=O)—; and X is either not present or $C_1$-$C_7$-alkylene, with the proviso that a heterocyclic radical $R_3$ is bonded via a ring carbon atom if X is not present;

or a salt of the said compounds.

The general terms used hereinbefore and hereinafter preferably have within the context of this disclosure the following meanings, unless otherwise indicated:

Where the plural form is used for compounds, salts, and the like, this is taken to mean also a single compound, salt, or the like.

Where compounds of formula I are mentioned which can form tautomers, it is meant to include also the tautomers of such compounds of formula I. In particular, tautomerism occurs e.g. for compounds of formula I which contain a 2-hydroxy-pyridyl radical (see e.g. radical $R_3$ of the below-mentioned Examples 115-120). In such compounds the 2-hydroxy-pyridyl radical can also be present as pyrid-2(1H)-on-yl.

Asymmetric carbon atoms of a compound of formula I that are optionally present may exist in the (R), (S) or (R,S) configuration, preferably in the (R) or (S) configuration. Substituents at a double bond or a ring may be present in cis-(=Z-) or trans (=E-) form. The compounds may thus be present as mixtures of isomers or preferably as pure isomers.

Preferably alkyl contains up to 20 carbon atoms and is most preferably lower alkyl.

The prefix "lower" denotes a radical having up to and including a maximum of 7, especially up to and including a maximum of 4 carbon atoms, the radicals in question being either unbranched or branched with single or multiple branching.

Lower alkyl is, for example, methyl, ethyl, n-propyl, iso-propyl, n-butyl, isobutyl, sec-butyl, tert-butyl, n-pentyl, iso-pentyl, neopentyl, n-hexyl or n-heptyl.

Alkyl $R_1$ and $R_2$ independently of each other are preferably methyl, ethyl, isopropyl or tert-butyl, especially methyl or ethyl.

Lower alkyl Y is preferably methyl, ethyl or propyl.

Lower alkoxy is for example ethoxy or methoxy, especially methoxy.

Substituted alkyl is preferably lower alkyl as defined above where one or more, preferably one, substituents may be present, such as e.g. amino, N-lower alkylamino, N,N-di-lower alkylamino, N-lower alkanoylamino, N,N-di-lower alkanoylamino, hydroxy, lower alkoxy, lower alkanoyl, lower alkanoyloxy, cyano, nitro, carboxy, lower alkoxycarbonyl, carbamoyl, N-lower alkyl-carbamoyl, N,N-di-lower alkyl carbamoyl, amidino, guanidino, ureido, mercapto, lower alkylthio, halogen or a heterocyclic radical.

Substituted alkyl $R_1$ and $R_2$ are independently of each other preferably hydroxy-lower alkyl, N,N-di-lower alkylamino-lower alkyl or morpholinyl-lower alkyl.

Preferably unsubstituted or substituted cycloalkyl $R_1$ or $R_2$ contains from 3 up to 20 carbon atoms and is especially unsubstituted or also substituted $C_3$-$C_5$ cycloalkyl wherein the substituents are selected from e.g. unsubstituted or substituted lower alkyl, amino, N-lower alkylamino, N,N-di-lower alkylamino, N-lower alkanoylamino, N,N-di-lower alkanoylamino, hydroxy, lower alkoxy, lower alkanoyl, lower alkanoyloxy, cyano, nitro, carboxy, lower alkoxycarbonyl, carbamoyl, N-lower alkyl-carbamoyl, N,N-di-lower alkyl-carbamoyl, amidino, guanidino, ureido, mercapto, lower alkylthio, halogen or a heterocyclic radical.

Mono- or disubstituted amino is amino substituted by one or two radicals selected independently of one another from e.g. unsubstituted or substituted lower alkyl.

Disubstituted amino $R_4$ is preferably N,N-di-lower alkylamino, especially N,N-dimethylamino or N,N-diethylamino.

A heterocyclic radical contains especially up to 20 carbon atoms and is preferably a saturated or unsaturated monocyclic radical having from 4 or 8 ring members and from 1 to 3 heteroatoms which are preferably selected from nitrogen, oxygen and sulfur, or a bi- or tri-cyclic radical wherein, for example, one or two carbocyclic radicals, such as e.g. benzene radicals, are annellated (fused) to the mentioned monocyclic radical. If a heterocyclic radical contains a fused carbocydic radical then the heterocyclic radical may also be attached to the rest of the molecule of formula I via a ring atom of the fused carbocydic radical. The heterocyclic radical (including the fused carbocyclic radical(s) if present) is optionally substituted by one or more, preferably by one or two, radicals such as e.g. unsubstituted or substituted lower alkyl, amino, N-lower alkylamino, N,N-di-lower alkylamino, N-lower alkanoylamino, N,N-di-lower alkanoylamino, hydroxy, lower alkoxy, lower alkanoyl, lower alkanoyloxy, cyano, nitro, carboxy, lower alkoxycarbonyl, carbamoyl, N-lower alkyl-carbamoyl, N,N-di-lower alkyl-carbamoyl, amidino, guanidino, ureido, mercapto, lower alkylthio, or halogen.

Most preferably a heterocyclic radical is pyrrolidinyl, piperidyl, lower alkyl-piperazinyl, di-lower alkyl-piperazinyl, morpholinyl, tetrahydropyranyl, pyridyl, pyridyl substituted by hydroxy or lower alkoxy, or benzodioxolyl, especially pyrrolidinyl, piperidyl, lower alkyl-piperazinyl, di-lower alkyl-piperazinyl or morpholinyl.

A heterocyclic radical $R_1$ or $R_2$ is as defined above for a heterocyclic radical with the proviso that it is bonded to the rest of the molecule of formula I via a ring carbon atom. Preferably a heterocyclic radical $R_1$ or $R_2$ is lower alkyl-piperazinyl or especially preferred tetrahydropyranyl. If one of the two radicals $R_1$ and $R_2$ represents a heterocyclic radical, the other is preferably hydrogen.

A heterocyclic radical $R_3$ is as defined above for a heterocyclic radical with the proviso that it is bonded to Q via a ring carbon atom if X is not present. Preferably a heterocyclic radical $R_3$ is benzodioxolyl, pyridyl substituted by hydroxy or lower alkoxy, or especially preferred indolyl substituted by halogen and lower alkyl. If $R_3$ is pyridyl substituted by hydroxy then the hydroxy group is preferably attached to a ring carbon atom adjacent to the ring nitrogen atom.

A heterocyclic radical $R_4$ is as defined above for a heterocyclic radical and is preferably pyrrolidinyl, piperidyl, lower alkyl-piperazinyl, morpholinyl or pyridyl.

If $R_1$ and $R_2$ together with the nitrogen atom to which they are attached form a heterocyclic radical, the heterocyclic radical is as defined above for a heterocyclic radical and represents preferably pyrrolidinyl, piperidyl, lower alkyl-piperazinyl, di-lower alkyl-piperazinyl or morpholinyl.

An unsubstituted or substituted aromatic radical $R_3$ has up to 20 carbon atoms and is unsubstituted or substituted, for example in each case unsubstituted or substituted phenyl.

Preferably an unsubstituted aromatic radical $R_3$ is phenyl. A substituted aromatic radical $R_3$ is preferably phenyl substituted by one or more substituents selected independently of one another from the group consisting of unsubstituted or substituted lower alkyl, amino, N-lower alkylamino, N,N-di-lower alkylamino, N-lower alkanoylamino, N,N-di-lower alkanoylamino, hydroxy, lower alkoxy, lower alkanoyl, lower alkanoyloxy, cyano, nitro, carboxy, lower alkoxycarbonyl, carbamoyl, N-lower alkyl-carbamoyl, N,N-di-lower alkyl-carbamoyl, amidino, guanidino, ureido, mercapto, lower alkylthio and halogen. Most preferably a substituted aromatic radical $R_3$ is phenyl substituted by one or more radicals selected independently of one another from the group consisting of lower alkyl, amino, hydroxy, lower alkoxy, halogen and benzyloxy.

Halogen is primarily fluoro, chloro, bromo or iodo, especially fluoro, chloro or bromo.

$C_1$-$C_7$-alkylene may be branched or unbranched and is in particular $C_1$-$C_3$-alkylene.

$C_1$-$C_7$-alkylene G is preferably $C_1$-$C_3$-alkylene, most preferably methylene (—$CH_2$—).

If G is not $C_1$-$C_7$-alkylene it preferably represents —C(=O)—.

$C_1$-$C_7$-alkylene X is preferably $C_1$-$C_3$-alkylene, most preferably methylene (—$CH_2$—) or ethan-1,1-diyl (—CH($CH_3$)—).

Q is preferably —NH—.

Z is preferably oxygen or sulfur, most preferably oxygen.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts.

In the presence of negatively charged radicals, such as carboxy or sulfo, salts may also be formed with bases, e.g. metal or ammonium salts, such as alkali metal or alkaline earth metal salts, or ammonium salts with ammonia or suitable organic amines, such as tertiary monoamines.

In the presence of a basic group and an acid group in the same molecule, a compound of formula I may also form internal salts.

For isolation or purification purposes it is also possible to use pharmaceutically unacceptable salts, for example picrates or perchlorates. Only the pharmaceutically acceptable salts or free compounds (if the occasion arises, in the form of pharmaceutical compositions) attain therapeutic use, and these are therefore preferred.

In view of the close relationship between the novel compounds in free form and in the form of their salts, including those salts that can be used as intermediates, for example in the purification or identification of the novel compounds, hereinbefore and hereinafter any reference to the free compounds is to be understood as referring also to the corresponding salts, as appropriate and expedient.

The compounds of formula I have valuable, pharmacologically useful properties. In particular they exhibit specific inhibitory activities that are of pharmacological interest. They are effective especially as protein tyrosine kinase inhibitors and/or (furthermore) as inhibitors of serine/threonine protein kinases; they exhibit, for example, powerful inhibition of the tyrosine kinase activity of the epidermal growth factor receptor (EGF-R) and of ErbB-2 kinase. These two protein tyrosine kinase receptors, together with their family members ErbB-3 and ErbB-4, play a key role in signal transmission in a large number of mammalian cells, including human cells, especially epithelial cells, cells of the immune system and cells of the central and peripheral nervous system. For example, in various cell types, EGF-induced activation of receptor-associated protein tyrosine kinase is a prerequisite for cell division and hence for the proliferation of the cell population. Most importantly, overexpression of the EGF-R (HER-1) and/or ErbB-2 (HER-2) has been observed in substantial fractions of many human tumours. EGF-R, e.g., was found to be overexpressed in non small-cell lung cancers, squameous carcinoma (head and neck), breast, gastric, ovarian, colon and prostate cancers as well as in gliomas. ErbB-2 was found to be overexpressed in squameous carcinoma (head and neck), breast, gastric, and ovarian cancers as well as in gliomas.

In addition to inhibiting the tyrosine kinase activity of the EGF-R, the compounds of formula I also inhibit to varying extents other protein tyrosine kinases that are involved in signal transmission mediated by trophic factors, specially the vascular endothelial growth factor (VEGF) receptor family (e.g. KDR, Flt-1, Flt-3) but also abl kinase, especially v-abl, kinases from the family of Src, especially c-Src, Lck and Fyn, the other members of the EGF receptor family such as ErbB-3 (HER-3) and ErbB-4 (HER-4), CSF-1, Kit, FGF receptor and the cyclin-dependent kinases CDK1 and CDK2, all of which play a part in growth regulation and transformation in mammalian cells, including human cells.

The inhibition of EGF-R tyrosine kinase activity can be demonstrated using known methods, for example using the recombinant intracellular domain of the EGF-receptor [EGF-R ICD; see, for example, E. McGlynn et al., Europ. J. Biochem. 207, 265-275 (1992)]. Compared with the control without inhibitor, the compounds of formula I inhibit the enzyme activity by 50% ($IC_{50}$), for example in a concentration of from 0.0005 to 0.5 µM, especially from 0.001 to 0.1 µM.

As well as or instead of inhibiting EGF-R tyrosine kinase activity, the compounds of formula I also inhibit other members of this family of receptors, like ErbB-2. The inhibitory activity ($IC_{50}$) is approximately in the range of 0.001 to 0.5 µM. The inhibition of ErbB-2 tyrosine kinase (HER-2) can be determined, for example, analogously to the method used for EGF-R protein tyrosine kinase [see C. House et al., Europ. J. Biochem. 140, 363-367 (1984)]. The ErbB-2 kinase can be isolated, and its activity determined, by means of protocols known per se, for example in accordance with T. Akiyama et al., Science 232, 1644 (1986).

Surprisingly, the compounds of formula I especially also inhibit the tyrosine kinase activity of the VEGF receptor family very potently. The compounds of the present invention are therefore very effective dual inhibitors of EGF- and VEGF-receptor family members. For inhibition of KDR and Flt-1 and inhibition of growth factor-induced proliferation of HUVECS see J. Wood et al., Cancer Res. 60, 2178-2189 (2000). The compounds of formula I inhibit e.g. the KDR tyrosine kinase activity with an $IC_{50}$ of from about 1 nM to about 1 µM, especially from about 5 nM to about 0.5 µM.

The action of the compounds of formula I on EGF-induced phosphorylation of the EGF-R can be determined in the human A431 epithelial carcinoma cell line by means of an ELISA which is described in U. Trnks et al., J. Med. Chem. 37:7, 1015-1027 (1994). In that test (EGF-R ELISA) the compounds of formula I exhibit an $IC_{50}$ of approximately from 0.001 to 1 µM.

The compounds of formula I potently inhibit the growth of EGF-R overexpressing NCI-H596 non-small cell lung carcinoma cells [see e.g. W. Lei, et al., Anticancer Res. 19(1A), 221-228 (1999)] at an $IC_{50}$ of approximately 0.01 to 1 µM. In the same range of activity, the compounds of formula I also potently inhibit the growth of ErbB2-overexpressing BT474 human breast cancer cells. The test procedures are adapted from T. Meyer et al., Int. J. Cancer 43, 851 (1989). The inhibitory activity of the compounds of formula I is determined, briefly, as follows: NCI-H596 cells (10 000/microtitre plate well) are transferred to 96-well microtitre plates. The test compounds [dissolved in dimethyl sulfoxide (DMSO)] are added in a series of concentrations (dilution series) in such a manner that the final concentration of DMSO is not greater than 1% (v/v). After the addition, the plates are incubated for three days during which the control cultures without test compound are able to undergo at least three cell-division cycles. The growth of the NCI-H596 cells is measured by means of methylene blue staining: after the incubation the cells are fixed with glutaraldehyde, washed with water and stained with 0.05% methylene blue. After a washing step the stain is eluted with 3% HCl and the optical density (OD) per well of the microtitre plate is measured using a Titertek Multiskan (Titertek, Huntsville, Ala., USA) at 665 nm. $IC_{50}$ values are determined by a computer-aided system using the formula:

$$IC_{50}=[(OD_{test}-OD_{start})/(OD_{control}-OD_{start})]\times 100.$$

The $IC_{50}$ value in those experiments is given as that concentration of the test compound in question that results in a cell count that is 50% lower than that obtained using the control without inhibitor. The compounds of formula I exhibit inhibitory activity with an IC50 in the range from approximately 0.01 to 1 µM.

The compounds of formula I exhibit inhibition of the growth of tumour cells also in vivo, as shown, for example, by the test described below: the test is based on inhibition of the growth of the human squamous lung carcinoma cell line NCI-H596 [ATCC HTB 178; American Type Culture Collection, Rockville, Md., USA; see Santon, J. B., et al., Cancer Research 46, 4701-4705 (1986) and Ozawa, S., et al., Int. J. Cancer 40, 706-710 (1987)], which is transplanted into female BALB/c nude mice (Bomholtgard, Denmark). That carcinoma exhibits a growth that correlates with the extent of the expression of the EGF-R. Tumours are established after subcutaneous (s.c.) injection of cells [a minimum of $2\times10^6$ cells in 100 µl phosphate-buffered saline (PBS) or medium] in carrier mice (4-8 mice). Injections are made s.c. in the left flank of the mouse mid-way between the tail and the head. The resulting tumours are serially passaged for a minimum of three consecutive transplantations prior to start of the treatment. During this time tumour growth rates stabilize. Tumours are not passaged more than 12 times. For the therapy experiment tumour fragments of roughly 25 mg are transplanted s.c. into the left flank of the animals using a 13-gauge trocar needle under Forene® (Abbott, Schwitzerland) anesthesia. Tumour growth and body weights are monitored twice per week. All treatments are initiated when the tumour attains a volume of 100 to 250 mm³. The tumour volumes are calculated using the known formula Length×Diameter²×π/6 [see Evans, B. D., et al., Brit. J. Cancer 45, 466-8 (1982)]. Anti-tumour activity is expressed as T/C % (mean increase of tumour volumes of treated animals divided by the mean increase of tumour volumes of control animals multiplied by 100%). At a dose of from 3 to 100 mg/kg of active ingredient, distinct inhibition of the tumour growth is found, for example T/C % values of less than 50.

The compounds of formula I may inhibit other protein tyrosine kinases that are involved in signal transmission mediated by trophic factors, for example abl kinase, such as especially v-abl kinase ($IC_{50}$ for example from 0.01 to 5 µM), kinases from the family of the src kinases, such as especially c-src kinase ($IC_{50}$ for example from 0.1 to 10 µM) and serine/threonine kinases, for example protein kinase C, all of which are involved in growth regulation and transformation in mammalian cells, including human cells.

The above-mentioned inhibition of v-abl tyrosine kinase is determined by the methods of N. Lydon et al., Oncogene Research 5, 161-173 (1990) and J. F. Geissler et al., Cancer Research 52, 4492-4498 (1992). In those methods [Val⁵]-angiotensin II and [γ-$^{32}$P]-ATP are used as substrates.

The compounds of formula I which inhibit the tyrosine kinase activity of the EGF-R or of the other protein tyrosine kinases mentioned are therefore useful, for example, in the treatment of benign or malignant tumours. The compounds of formula I are e.g. able to simultaneously inhibit the growth of tumors with deregulated EGF-R and/or ErbB-2 activity as well as to inhibit the vascularisation of solid tumors triggered by VEGF. This combined activity leads to an improved anti-tumour effect. (see also WO 02/41882). Moreover, the use of a dual inhibitor reduces the risk of drug-drug interactions and further reduces the total drug load as compared to a combination therapy. The compounds of formula I are capable of slowing down tumor growth or effecting tumour regression and of preventing the formation of tumour metastases and the growth of micrometastases. They can be used especially in the case of epidermal hyperproliferation (psoriasis), in the treatment of neoplasias of epithelial character, e.g. mammary carcinomas, and in leukaemias. In addition, the compounds of formula I can be used in the treatment of those disorders of the immune system in which several or, especially, individual protein tyrosine kinases and/or (furthermore) serine/threonine protein kinases are involved; the compounds of formula I can also be used in the treatment of those disorders of the central or peripheral nervous system in which signal transmission by several or, especially, a single protein tyrosine kinase(s) and/or (furthermore) serine/threonine protein kinase(s) is/are involved.

In general, the present invention relates also to the use of the compounds of formula I for the inhibition of the mentioned protein kinases, in particular to their use for the dual inhibition of EGF- and VEGF-receptor family members.

The compounds according to the invention can be used both alone and in combination with other pharmacologically active compounds, for example together with inhibitors of the enzymes of polyamine synthesis, inhibitors of protein kinase C, inhibitors of other tyrosine kinases, cytokines, negative growth regulators, for example TGF-β or IFN-β, aromatase inhibitors, antioestrogens and/or cytostatic drugs.

With the groups of preferred compounds of formula I mentioned hereinafter, definitions of substituents from the general definitions mentioned hereinbefore may reasonably be used, for example, to replace more general definitions with more specific definitions or especially with definitions characterized as being preferred.

Preference is given to a compound of formula I, wherein $R_1$ and $R_2$ are each independently of the other hydrogen, unsubstituted or substituted alkyl or cycloalkyl, a heterocyclic radical bonded via a ring carbon atom, or a radical of the formula $R_4$—Y—(C=Z)— wherein $R_4$ is unsubstituted, mono- or disubstituted amino or a heterocyclic radical, Y is either not present or lower alkyl and Z is oxygen or sulfur or imino, with the proviso that $R_1$ and $R_2$ are not both hydrogen; or $R_1$ and $R_2$ together with the nitrogen atom to which they are attached form a heterocyclic radical;

$R_3$ is a heterocyclic radical or an unsubstituted or substituted aromatic radical;

G is $C_1$-$C_7$-alkylene;

Q is —NH— or —O—; and

X is either not present or $C_1$-$C_7$-alkylene, with the proviso that a heterocyclic radical $R_3$ is bonded via a ring carbon atom if X is not present;

or a salt thereof.

Preference is further given to a compound of formula I, wherein $R_1$ and $R_2$ are each independently of the other hydrogen, unsubstituted or substituted alkyl or cycloalkyl, a heterocyclic radical bonded via a ring carbon atom, or a radical of the formula $R_4$—Y—(C=Z)— wherein $R_4$ is unsubstituted, mono- or disubstituted amino or a heterocyclic radical, Y is either not present or lower alkyl and Z is oxygen, sulfur or imino, with the proviso that $R_1$ and $R_2$ are not both hydrogen; or $R_1$ and $R_2$ together with the nitrogen atom to which they are attached form a heterocyclic radical;

$R_3$ is a heterocyclic radical or an unsubstituted or substituted aromatic radical;

G is $C_1$-$C_7$-alkylene;

Q is —NH—; and

X is either not present or $C_1$-$C_7$-alkylene, with the proviso that a heterocyclic radical $R_3$ is bonded via a ring carbon atom if X is not present;

or a salt thereof.

Special preference is given to a compound of formula I, wherein $R_1$ and $R_2$ are each independently of the other hydrogen, unsubstituted or substituted lower alkyl or $C_3$-$C_6$ cycloalkyl, a heterocyclic radical bonded via a ring carbon atom and containing up to 20 carbon atoms, or a radical of the formula $R_4$—Y—(C=Z)— wherein $R_4$ is unsubstituted, mono- or disubstituted amino or a heterocyclic radical containing up to 20 carbon atoms, Y is either not present or lower alkyl and Z is oxygen, with the proviso that $R_1$ and $R_2$ are not both hydrogen; or $R_1$ and $R_2$ together with the nitrogen atom to which they are attached form a heterocydic radical containing up to 20 carbon atoms;

$R_3$ is a heterocyclic radical containing up to 20 carbon atoms or an unsubstituted or substituted aromatic radical having up to 20 carbon atoms;

G is $C_1$-$C_3$-alkylene;

Q is —NH—; and

X is either not present or $C_1$-$C_3$-alkylene, with the proviso that a heterocyclic radical $R_3$ is bonded via a ring carbon atom if X is not present;

or a salt thereof.

Special preference is further given to a compound of formula I, wherein $R_1$ and $R_2$ are each independently of the other hydrogen, lower alkyl, hydroxy-lower alkyl, N,N-di-lower alkylamino-lower alkyl, morpholinyl-lower alkyl, tetrahydropyranyl, or a radical of the formula $R_4$—Y—(C=Z)— wherein $R_4$ is di-lower alkylamino, pyrrolidinyl, piperidyl, lower alkyl-piperazinyl, morpholinyl or pyridyl, Y is either not present or lower alkyl and Z is oxygen, with the proviso that $R_1$ and $R_2$ are not both hydrogen; or $R_1$ and $R_2$ together with the nitrogen atom to which they are attached form a radical selected from the group consisting of pyrrolidinyl, piperidyl, lower alkyl-piperazinyl, di-lower alkyl-piperazinyl and morpholinyl;

$R_3$ is phenyl, benzodioxolyl, pyridyl substituted by hydroxy or lower alkoxy, indolyl substituted by halogen and lower alkyl, or phenyl substituted by one or more radicals selected independently of one another from the group consisting of lower alkyl, hydroxy, lower alkoxy, halogen and benzyloxy;

G is —$CH_2$— or —C(=O)—;

Q is —NH— or —O—, with the proviso that Q is —O— if G is —C(=O)—; and

X is either not present, —$CH_2$— or —$CH(CH_3)$—, with the proviso that substituted pyridyl or indolyl $R_3$ is bonded via a ring carbon atom if X is not present;

or a salt thereof.

Special preference is further also given to a compound of formula I, wherein $R_1$ and $R_2$ are each independently of the other hydrogen, lower alkyl, hydroxy-lower alkyl or a radical of the formula $R_4$—Y—(C=Z)— wherein $R_4$ is di-lower alkylamino, pyrrolidinyl, piperidyl, lower alkyl-piperazinyl, morpholinyl or pyridyl, Y is either not present or lower alkyl and Z is oxygen, with the proviso that $R_1$ and $R_2$ are not both hydrogen; or $R_1$ and $R_2$ together with the nitrogen atom to which they are attached form a radical selected from the group consisting of pyrrolidinyl, piperidyl, lower alkyl-piperazinyl, di-lower alkyl-piperazinyl and morpholinyl;

$R_3$ is phenyl, benzodioxolyl, pyridyl substituted by hydroxy or lower alkoxy, or phenyl substituted by one or more radicals selected independently of one another from the group consisting of lower alkyl, hydroxy, lower alkoxy, halogen and benzyloxy;

G is —$CH_2$—;

Q is —NH—; and

X is either not present, —$CH_2$— or —$CH(CH_3)$—, with the proviso that substituted pyridyl $R_3$ is bonded via a ring carbon atom if X is not present;

or a salt thereof.

Special preference is also given to a compound of formula I wherein $C_1$-$C_7$-alkylene G is attached to the phenyl ring at position 3 or 4, most especially at position 4.

Very special preference is further given to a compound of formula I mentioned in the Examples below, or a salt, especially a pharmaceutically acceptable salt, thereof.

Also especially preferred are compounds of formula I, which—according to the above described tyrosine kinase inhibition assays—inhibit HER-1, HER-2 and KDR with $IC_{50}$ values of less than 300 nM, most preferably of less than 100 nM.

Very special preference is further given to compounds of formula I which inhibit the tyrosine kinase activity of at least one member of the EGF receptor family together with at least one member of the VEGF receptor family (dual inhibition of EGF- and VEGF-receptor family members) with $IC_{50}$ values in the range of 0.5 nM to 0.5 μM, especially in the range of 1 nM to 300 nM, based on the above-described tyrosine kinase inhibition assays.

Especially preferred are further also compounds of formula I in which G is $C_1$-$C_7$-alkylene since the amine group of such compounds allows to generate pharmaceutically acceptable salts of these compounds which in general leads to an increased solubility and to improved physico-chemical properties.

The compounds of formula I or salts thereof are prepared in accordance with processes known per se (see also EP 682 027, WO 97/02266, WO 97/27199 and WO 98/07726), though not previously described for the manufacture of the compounds of the formula I, especially whereby a) in order to prepare a compound of formula I, wherein G is $C_1$-$C_7$-alkylene and wherein $R_1$ and $R_2$ are each independently of the other hydrogen, unsubstituted or substituted alkyl or cycloalkyl, or a heterocyclic radical bonded via a ring carbon atom, with the proviso that $R_1$ and $R_2$ are not both hydrogen, or wherein $R_1$ and $R_2$ together with the nitrogen atom to which they are attached form a heterocyclic radical, a compound of the formula II

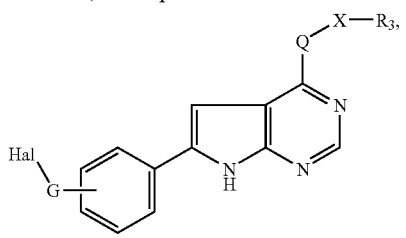

(II)

wherein Hal is halogen, G is $C_1$-$C_7$-alkylene and $R_3$, Q and X have the meanings as defined for a compound of formula I, is reacted with a compound of the formula III

(III)

wherein $R_1$ and $R_2$ are each independently of the other hydrogen, unsubstituted or substituted alkyl or cycloalkyl, or a heterocyclic radical bonded via a ring carbon atom, with the proviso that $R_1$ and $R_2$ are not both hydrogen, or wherein $R_1$ and $R_2$ together with the nitrogen atom to which they are attached form a heterocyclic radical;

b) in order to prepare a compound of formula I, wherein G is $C_1$-$C_7$-alkylene and wherein $R_1$ is a radical of the formula $R_4$—Y—(C=Z)— wherein $R_4$ is unsubsbtuted, mono- or disubstituted amino or a heterocyclic radical, Y is either not present or lower alkyl and Z is oxygen or sulfur, (i) a compound of the formula IV

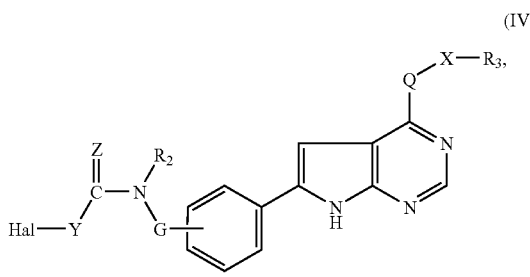

(IV)

wherein Hal is halogen, G is $C_1$-$C_7$-alkylene, Z is oxygen and the remaining substituents and symbols have the meanings as defined for a compound of formula I according to claim 1, is reacted with a compound of the formula $R_4$—H wherein $R_4$ is unsubstituted, mono- or disubstituted amino or a heterocyclic radical containing at least one nitrogen ring atom wherein the heterocyclic radical is attached to the hydrogen atom of $R_4$—H via a nitrogen ring atom, or (ii) a compound of the formula V

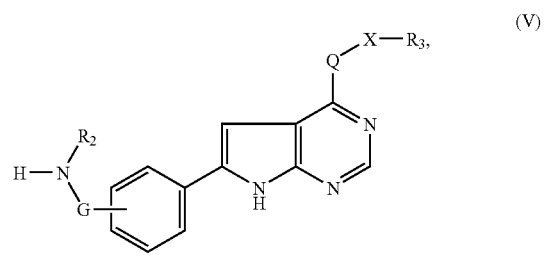

(V)

wherein G is $C_1$-$C_7$-alkylene and the remaining substituents and symbols have the meanings as defined for a compound of formula I, is reacted with a compound of the formula VI

(VI)

wherein $R_4$ and Y have the meanings as defined above under formula I and Z is oxygen, whereby a compound of formula I which results from process b) (i) or (ii) is optionally converted into the respective compound wherein Z is sulfur;

c) in order to prepare a compound of formula I, wherein G is —C(=O)— or $C_1$-$C_6$-alkylene-C(=O)— wherein the carbonyl group is attached to the $NR_1R_2$ moiety, a compound of formula XI

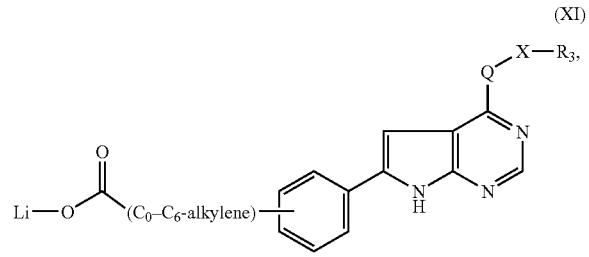

(XI)

wherein the substituents and symbols have the meanings as defined for a compound of formula I, is reacted with a compound of formula XII

(XII)

wherein $R_1$ and $R_2$ have the meanings as defined for a compound of formula I; or d) in order to prepare a compound of formula I, wherein G is $C_1$-$C_7$-alkylene, a compound of formula I, wherein G is —C(=O)— or $C_1$-$C_6$-alkylene-C(=O)— wherein the carbonyl group is attached to the $NR_1R_2$ moiety, is reacted with a reducing agent to produce the corresponding compound in which G is $C_1$-$C_7$-alkylene;

whereby functional groups which are present in the starting compounds of processes a) to d) and are not intended to take part in the reaction, are present in protected form if necessary, and protecting groups that are present are cleaved, whereby the said starting compounds may also exist in the form of salts provided that a salt-forming group is present and a reaction in salt form is possible;

and, if so desired, a compound of formula I thus obtained is converted into another compound of formula I, a free compound of formula I is converted into a salt, an obtained salt of a compound of formula I is converted into the free compound or another salt, and/or a mixture of isomeric compounds of formula I is separated into the individual isomers.

Description of the Process Variants:

Regarding Process a):

The reaction between a compound of formula II and a compound of formula III preferably takes place in a suitable inert solvent, especially N,N-dimethylformamide, in the presence of a base such as potassium carbonate, at temperatures from room temperature (RT) to 100° C. Alternatively, the reaction between a compound of formula II and a compound of formula III takes place in a suitable solvent, e.g. lower alcohols, such as ethanol, in the presence of for example a suitable catalyst such as NaL, preferably at the reflux temperature of the solvent employed. In a compound of formula II, Hal is preferably chloro.

Regarding Process b):

(i) The reaction of a compound of formula IV and a compound of the formula $R_4$—H preferably takes place in a suitable solvent, especially alcohols, e.g. lower alcohols such as n-butanol, at elevated temperature, preferably near the boiling temperature of the solvent employed. In a compound of formula IV, Hal is preferably chloro.

(ii) The reaction between a compound of formula V and a compound of formula VI preferably takes place in the presence of O-(1,2-dihydro-2-oxo-1-pyridyl)-N,N,N'N'-tetramethyluronium-tetrafluroborate (TPTU) and N,N-diisopropylethylamine, or in the presence of (benzotriazole-1-yloxy)-tris-(dimethylamino)-phosphonium-hexafluoroborate (BOP) and N-methylmorpholin, in a suitable inert solvent, such as for example N,N-dimethylformamide, preferably at RT.

A compound of formula I which results from process b) (i) or (ii) can be converted into the respective compound of formula I wherein Z is sulfur, for example, by using an appropriate sulfur compound, e.g. using reaction with Lawesson's reagent (2,4-bis-(4-methoxyphenyl)2,4-dithioxo-1,2,3,4-dithia-phosphetan) in a halogenated carbon hydrate, such as dichloromethane, or an aprotic solvent, such as toluene or xylene, at temperatures from about 30° C. to reflux.

Regarding Process c):

The reaction of a compound of formula XI with a compound of formula XII preferably takes place in a suitable inert solvent such as N,N-dimethylformamide and in an inert, for example an argon or nitrogen, atmosphere, in the presence of diethyl-cyanphosphonate, preferably at about 0° C.

Regarding process d):

The reducing agent used in process d) is preferably lithium aluminium hydride or diisobutyl-aluminium hydride. The reaction preferably takes place under those conditions described in Example 79 or 141, respectively.

Additional Process Steps

In the additional process steps, carried out as desired, functional groups of the starting compounds which should not take part in the reaction may be present in unprotected form or may be protected for example by one or more protecting groups. The protecting groups are then wholly or partly removed according to one of the known methods. Protecting groups, and the manner in which they are introduced and removed are described, for example, in "Protective Groups in Organic Chemistry", Plenum Press, London, New York 1973, and in "Methoden der organischen Chemie". Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions.

The end products of formula I may however also contain substituents that can also be used as protecting groups in starting materials for the preparation of other end products of formula I. Thus, within the scope of this text, only a readily removable group that is not a constituent of the particular desired end product of formula I is designated a "protecting group", unless the context indicates otherwise.

General Process Conditions

All process steps described here can be carried out under known reaction conditions, preferably under those specifically mentioned, in the absence of or usually in the presence of solvents or diluents, preferably those that are inert to the reagents used and able to dissolve them, in the absence or presence of catalysts, condensing agents or neutralising agents, for example ion exchangers, typically cation exchangers, for example in the $H^+$ form, depending on the type of reaction and/or reactants at reduced, normal, or elevated temperature, for example in the range from −100° C. to about 190° C., preferably from about −80° C. to about 150° C., for example at −80 to −60° C., at RT, at −20 to 40° C., at 0 to 100° C. or at the boiling point of the solvent used, under atmospheric pressure or in a closed vessel, if need be under pressure, and/or in an inert, for example an argon or nitrogen, atmosphere.

The invention relates also to those embodiments of the process in which one starts from a compound obtainable at any stage as an intermediate and carries out the missing steps, or breaks off the process at any stage, or forms a starting material under the reaction conditions, or uses said starting material in the form of a reactive derivative or salt, or produces a compound obtainable by means of the process according to the invention under those process conditions, and further processes the said compound in situ. In the preferred embodiment, one starts from those starting materials which lead to the compounds described hereinabove as preferred.

In the preferred embodiment, a compound of formula I is prepared according to the processes and process steps defined in the Examples.

The compounds of formula I, including their salts, are also obtainable in the form of hydrates, or their crystals can include for example the solvent used for crystallisation (present as solvates).

Starting Materials

New starting materials and/or intermediates, as well as processes for the preparation thereof, are likewise the subject of this invention. In the preferred embodiment, such starting materials are used and reaction conditions so selected as to enable the preferred compounds to be obtained.

The starting materials used in the above described processes a) to b) are known, capable of being prepared according to known processes (see also EP 682 027, WO 97/02266, WO 97/27199 and WO 98/07726), or commercially obtainable; in particular, they can be prepared using processes as described in the Examples.

In the preparation of starting materials, existing functional groups which do not participate in the reaction should, if necessary, be protected. Preferred protecting groups, their introduction and their removal are described above or in the Examples. In place of the respective starting materials and transients, salts thereof may also be used for the reaction, provided that salt-forming groups are present and the reaction with a salt is also possible. Where the term starting materials is used hereinbefore and hereinafter, the salts thereof are always included, insofar as reasonable and possible.

A compound of formula II can be prepared for example by reacting a compound of formula VII

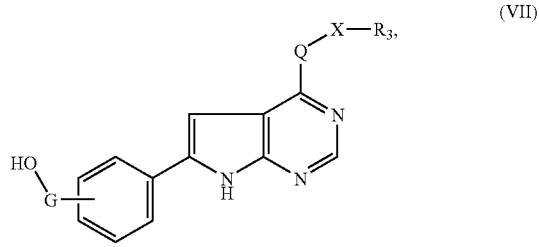

(VII)

wherein G is $C_1$-$C_7$-alkylene and $R_3$, Q and X have the meanings as defined for a compound of formula I, with e.g. thionyl halogenide, preferably thionyl choride, in the presence or absence of pyridine, in an inert solvent, for example toluene or in a 1:1 mixture of acetonitrile and dioxane, preferably at −10 to 0° C. or at RT.

A compound of formula VII can be prepared for example by reacting a compound of formula VIII

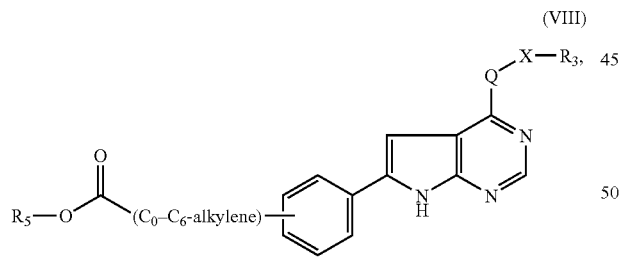

(VIII)

wherein $R_5$ is lower alkyl, especially methyl or ethyl, and $R_3$, Q and X have the meanings as defined for a compound of formula I, with lithium aluminium hydride, in an inert solvent, especially ethers, e.g. cyclic ethers such as tetrahydrofuran, preferably at the reflux temperature of the solvent employed. Alternatively, a compound of formula VII may be prepared by reacting a compound of formula VIII with diisobutyl-aluminium hydride, in an inert solvent, for example in tetrahydrofuran or in a 1:1 mixture of dichloromethane and dioxane, preferably at RT.

A compound of formula VIII wherein Q is —NH— can be prepared for example by reacting a compound of formula IX

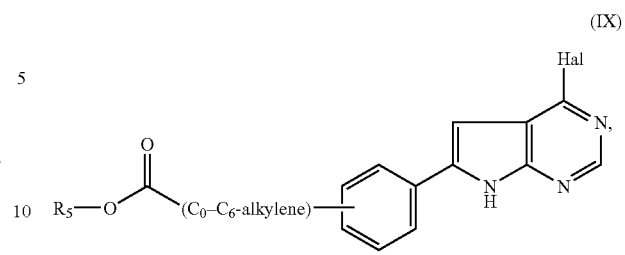

(IX)

wherein Hal is halogen, preferably chloro, and $R_5$ is as defined above for a compound of formula VIII, with a compound of the formula $H_2N$—X—$R_3$, wherein $R_3$ and X have the meanings as defined for a compound of formula I, (i) in a suitable solvent such as alcohols, especially lower alcohols such as n-butanol, preferably at the boiling temperature of the solvent employed or (ii) under catalytic conditions e.g. according to the Buchwald reaction conditions such as those described in Step 133.1 of Example 133 below.

A compound of formula VIII wherein Q is —O— can be prepared for example by reacting a compound of formula IX, which is preferably N-protected in the pyrrolo-pyrimidine moiety, with a compound of the formula HO—X—$R_3$, wherein $R_3$ and X have the meanings as defined for a compound of formula I, in a suitable inert solvent such as N,N-dimethylformamide and in the presence of a base such as potassium carbonate, at elevated temperatures, preferably at around 100° C.

Alternatively, the carboxylic acid ester of a compound of formula IX may first be reduced to the corresponding alcohol, e.g. under conditions described above for the preparation of a compound of formula VII, and then either be reacted with a compound of the formula $H_2N$—X—$R_3$, e.g. under conditions described above for the preparation of a compound of formula VIII wherein Q is —NH—, or be reacted with a compound of the formula HO—X—$R_3$, e.g. under conditions described above for the preparation of a compound of formula VIII wherein Q is —O—.

A compound of formula IV can be prepared for example by reacting a compound of formula V with a compound of the formula X

(X)

wherein Hal is Halogen, preferably chloro, Y has the meanings as defined above under formula I, and Z is oxygen, in the presence of triethylamine, in an inert solvent such as e.g. tetrahydrofuran, preferably at RT.

A compound of formula XI can be prepared for example by reacting a compound of formula VIII with LiOH, preferably in a mixture of dioxane and water, at elevated temperatures, preferably under those conditions described in Step 141.4 of Example 141 below.

The remaining starting materials are known, capable of being prepared according to known processes, or commercially available; or in particular, they can be prepared using processes as described in the Examples.

Pharmaceutical Compositions, Methods, and Uses

The present invention relates also to pharmaceutical compositions that comprise a compound of formula I, or a pharmaceutically acceptable salt thereof, as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions contain the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention also relates to prodrugs of a compound of formula I that convert in vivo to the compound of formula I as such. Any reference to a compound of formula I is therefore to be understood as referring also to the corresponding pro-drugs of the compound of formula I, as appropriate and expedient.

The invention relates also to compounds of formula I, or a pharmaceutically acceptable salt thereof, as such or in the form of a pharmaceutical composition, for use in a method for the prophylactic or especially therapeutic treatment of the human or animal body, to a process for the preparation thereof (especially in the form of compositions for the treatment of tumours) and to a method of treating proliferative diseases, primarily tumour diseases, especially those mentioned above.

The invention relates also to processes and to the use of compounds of formula I, or a pharmaceutically acceptable salt thereof, for the preparation of pharmaceutical compositions which comprise compounds of formula I, or a pharmaceutically acceptable salt thereof, as active component (active ingredient).

If desired, the said pharmaceutical compositions may also contain further active components, for example cytostatics, and/or may be used in combination with known therapeutic processes, for example the administration of hormones or radiation.

Preference is given for a pharmaceutical composition which is suitable for administration to a warm-blooded animal, especially humans or commercially useful mammals suffering from a disease which responds to an inhibition of a protein tyrosine kinase, especially to a dual inhibition of EGF- and VEGF-receptor family members, especially a neoplastic disease, comprising an effective quantity of a compound of formula I for the inhibition of a protein tyrosine kinase, especially for the dual inhibition of EGF- and VEGF-receptor family members, or a pharmaceutically acceptable salt thereof, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or especially therapeutically active against said diseases a compound of formula I, or a pharmaceutically acceptable salt thereof, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories or capsules. Examples are capsules containing from about 0.05 g to about 1.0 g of active substance.

The pharmaceutical compositions of the present invention are prepared in a manner known per se, for example by means of conventional mixing, granulating, coating, dissolving or lyophilising processes.

The invention relates likewise to a process or a method for the treatment of one of the pathological conditions mentioned hereinabove, especially a disease which responds to an inhibition of a protein tyrosine kinase, especially to a dual inhibition of EGF- and VEGF-receptor family members, especially a corresponding neoplastic disease. The compounds of formula I, or pharmaceutically acceptable salts thereof, can be administered as such or in the form of pharmaceutical compositions, prophylactically or therapeutically, preferably in an amount effective against the said diseases, to a warm-blooded animal, for example a human, requiring such treatment, the compounds especially being used in the form of pharmaceutical compositions. In the case of an individual having a bodyweight of about 70 kg the daily dose administered is from approximately 0.1 g to approximately 5 g, preferably from approximately 0.5 g to approximately 2 g, of a compound of the present invention.

The present invention relates especially also to the use of a compound of formula I, or a pharmaceutically acceptable salt thereof, especially a compound of formula I which is said to be preferred, or a pharmaceutically acceptable salt thereof, as such or in the form of a pharmaceutical composition with at least one pharmaceutically acceptable carrier, for the therapeutic and also prophylactic management of one or more of the diseases mentioned hereinabove, preferably a disease which responds to an inhibition of a protein tyrosine kinase, especially to a dual inhibition of EGF- and VEGF-receptor family members, especially a neoplastic disease, in particular if the said disease responds to an inhibition of a protein tyrosine kinase, especially to a dual inhibition of EGF- and VEGF-receptor family members.

The present invention relates especially also to the use of a compound of formula I, or a pharmaceutically acceptable salt thereof, especially a compound of formula I which is said to be preferred, or a pharmaceutically acceptable salt thereof, for the preparation of a pharmaceutical composition for the therapeutic and also prophylactic management of one or more of the diseases mentioned hereinabove, especially a neoplastic disease, in particular if the disease responds to an inhibition of a protein tyrosine kinase, especially to a dual inhibition of EGF- and VEGF-receptor family members.

A compound of formula I may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™. Aminoglutethimide can be administered, e.g., in the form as it is marketed, e.g. under the trademark ORIMETEN™. A combination of the invention comprising an antineoplastic agent which is an aromatase inhibitor is particularly useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be formulated as disclosed in U.S. Pat. No. 4,659,516 or it can be administered, e.g., in the form as it is marketed, e.g. under the trademark FASLODEX™.

The term "topoisomerase I inhibitors" as used herein includes, but is not limited to topotecan, irnotecan, 9-nitro-camptothecin and the macromolecular camptothecin conjugate PNU-166148 (compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™. Epirubicin can be administered, e.g., in the form as it is marketed, e.g. under the trademark FARMORUBICIN™. Idarubicin can be administered, e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity.

The term "farnestyl transferase inhibitors" relates to compounds which inhibit the farnesyl transferase and which possess antiproliferative activity.

The term "COX-2 inhibitors" relates to compounds which inhibit the cyclooxygenase type 2 enyzme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cisplatin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, Platelet-derived Growth Factor (PDGF), Bcr-Abl tyrosine kinase, c-kit, Flt-3 and Insulin-like Growth Factor I Receptor (IGF-IR) and Cyclin-dependent kinases (CDKs), and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958 (describing compounds of formula I), WO 00/09495, WO 00/27820, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00/37502 and WO 94/10202; Angiostatin™, described by M. S. O'Reilly et al, Cell 79, 1994, 315-328; and Endostatin™, described by M. S. O'Reilly et al, Cell 88, 1997, 277-285; compounds which decrease the activity of EGF are especially compounds which inhibit the EGF receptor, especially the tyrosine kinase activity of the EGF receptor, and compounds binding to EGF, and are in particular those compounds generically and specifically disclosed in WO 97/02266 (describing compounds of formula IV), EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980;

compounds which decrease the activity of c-Src include, but are not limited to, compounds inhibiting the c-Src protein tyrosine kinase activity as defined below and to SH2 interaction inhibitors such as those disclosed in WO97/07131 and WO97/08193;

compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrdo[2,3-d]pyrimidines. Preferably, the term relates to those compounds disclosed in WO 96/10028, WO 97/28161, WO97/32879 and WO97/49706;

compounds which decreases the activity of the protein kinase C are especially those staurosporine derivatives disclosed in EP 0 296 110 (pharmaceutical preparation described in WO 00/48571) which compounds are protein kinase C inhibitors;

further specific compounds that decrease protein kinase activity and which may also be used in combination with the compounds of the present invention are Imatinib (Gleevec®/Glivec®), PKC412, Iressa™ (ZD1839), PKI166, PTK787, ZD6474, GW2016, CHIR-200131, CEP-7055/CEP-5214, CP-547632 and KRN-633; anti-angiogenic compounds having another mechanism of action than decreasing the protein kinase activity include, but are not limited to e.g. thalidomide (THALOMID), celecoxib (Celebrex), SU5416 and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be formulated, eg. as disclosed in U.S. Pat. No. 5,843,901.

The term "anti-androgens" as used herein includes, but is not limited to bicalutamide (CASODEX™), which can be formulated, e.g. as disclosed in U.S. Pat. No. 4,636,505.

The term "bengamides" relates to bengamides and derivatives thereof having aniproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

The term "antiproliferative antibodies" as used herein includes, but is not limited to trastuzumab (Herceptint™), Trastuzumab-DM1, erlotinib (Tarceva™), bevacizumab (Avastin™), rituximab (Rituxan®), PRO64553 (anti-CD40) and 2C4 Antibody.

For the treatment of AML, compounds of formula I can be used in combination with standard leukemia therapies, especially in combination with therapies used for the treatment of AML. In particular, compounds of formula I can be administered in combination with e.g. farnesyltransferase inhibitors and/or other drugs used for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of formula I, can be prepared and administered as described in the art such as in the documents cited above.

EXAMPLES

The following Examples serve to illustrate the invention without limiting its scope.

Temperatures are measured in degrees Celsius. Unless otherwise indicated, the reactions take place at RT.

The $R_1$ values which indicate the ratio of the distance moved by each substance to the distance moved by the eluent front are determined on silica gel thin-layer plates (Merck, Darmstadt, Germany) by thin-layer chromatography using the respective named solvent systems.

If not otherwise indicated, the analytical HPLC conditions are as follows:

| | |
|---|---|
| Column: | (250 × 4.6 mm) packed with reversed-phase material C18-Nucleosil (5 μm mean particle size, with silica gel covalently derivatized with octadecylsilanes, Macherey & Nagel, Düren, Germany). Detection by UV absorption at 215 nm. The retention times ($t_R$) are given in minutes. Flow rate: 1 ml/min. |
| Gradient: | 20% → 100% a) in b) for 14 min + 5 min 100% a). |
| | a): Acetonitrile + 0.05% TFA; b): water + 0.05% TFA. |

The short forms and abbreviations used have the following definitions:

| | |
|---|---|
| conc. | concentrated |
| DMF | N,N-dimethylformamide |
| Elem. anal. | elemental analysis |
| Et | ethyl |
| EtOAc | ethyl acetate |
| MS-ES | mass spectroscopy (electron spray) |
| h | hour(s) |
| Me | methyl |
| MeOH | methanol |
| min | minute(s) |
| m.p. | melting point |
| RT | room temperature |
| TFA | trifluoroacetic acid |
| THF | tetrahydrofuran (distilled over Na/benzophenone) |
| TLC | thin-layer chromatography |
| $t_R$ | retention times |

Example 1

(3Chloro-4-fluoro-phenyl)-[6-(4-dimethylaminomethyl-phenyl)-7H-pyrrolo[2,3-d]pyrimidin-4-yl]-amine A mixture of 200 mg (0.5 mmol) crude (3-chloro-4-fluoro-phenyl)-[6-(4-chloromethyl-phenyl)-7H-pyrrolo[2,3-d]pyrimidin-4-yl]-amine in 15 ml absolute ethanol is treated with 0.8 ml (5 mmol) of a 33% solution of dimethylamine in ethanol (Fluka, Buchs, Switzerland) and then heated under reflux for 1 h. The almost clear solution is cooled and the solvent evaporated. The residue is dissolved in a mixture of dichloromethane and ethanol (95:5), washed with water, dried over sodium sulfate and the solvent evaporated. Purification of the crude material through flash chromatography using first dichloromethane/ethanol 95:5 plus 1% conc.

ammonia and then dichloromethane/ethanol 9:1 plus 1% conc. ammonia gives the title compound; m.p. 274-276° C.; MS-ES⁺: (M+H)⁺=396.

Step 1.1: 4-[4-(3-Chloro-4-fluoro-phenylamino)-7H-pyrrolo[2,3-d]pyrimidin-6-yl]-benzoic acid ethyl ester 3.6 g (12 mmol) 4-(4-Chloro-7H-pyrrolo[2,3-d]pyrimidin-6-yl)-benzoic acid ethyl ester (WO 97/02266) are suspended in 80 ml n-butanol and treated with 3.5 g (24 mmol) 3-chloro-4-fluoro-aniline. The mixture is heated to 145° C. under stirring. After 30 min a clear brown solution is obtained which turns into a thick suspension after 2 h. After a total of 3 h the reaction mixture is cooled in an ice bath and the product collected by filtration; m.p.>300° C.; $R_f$ (dichloromethane/ethanol 95:5 plus 1% conc. ammonia)=0.29; HPLC $t_R$=11.66 min.

Step 1.2: {4-[4-(3-Chloro-4-fluoro-phenylamino)-7H-pyrrolo[2,3-d]pyrimidin-6-yl]-phenyl}-methanol 570 mg (15 mmol) lithium aluminium hydride are suspended in 150 ml dry THF at RT. 4-[4-(3-Chloro-4-fluoro-phenylamino)-7H-pyrrolo[2,3-d]pyrimidin-6-yl]-benzoic acid ethyl ester (1.23 g, 3 mmol) are added and the resulting mixture is heated to reflux for 1 h. The mixture is cooled in an ice bath and treated sequentially with water (0.57 ml), 15% sodium hydroxide solution (0.57 ml) and water (1.71 ml). The solid aluminum complex is removed by filtration (Hyflo Super Cel®; Fluka, Buchs, Switzerland), the filtrate dried over sodium sulfate and the solvent evaporated. The residue was suspended in water, filtered and dried to give the title compound; m.p.>300° C.; HPLC $t_R$=9.14 min.

Step 1.3: (3-Chloro-4-fluoro-phenyl)-[6-(4-chloromethyl-phenyl)-7H-pyrrolo[2,3-d]pyrimidin-4-yl]-amine 184 mg (0.5 mmol) {4-[4-(3-Chloro-4-fluoro-phenylamino)-7H-pyrrolo[2,3-d]pyrimidin-6-yl]-phenyl}-methanol are suspended in 15 ml toluene. Pyridine (44 μl, 0.55 mmol) and thionyl chloride (40 μl, 0.55 mmol) are added and the mixture is stirred at RT for 16 h. A second portion of the same amounts of pyridine and thionyl chloride are then added and the mixture stirred for 1 additional hour. The solvent is evaporated and the residue suspended in water containing a small amount of sodium bicarbonate (pH~8). After filtration, the product was thoroughly washed with water and ether and dried to give crude title compound; m.p.>300° C.; $R_f$ (dichloromethane/ethanol 95:5 plus 1% conc. ammonia)=0.42; HPLC $t_R$=11.33 min.

Examples 2-8d

The following Examples are synthesized from (3-chloro-4-fluoro-phenyl)[6-(4-chloromethyl-phenyl)-7H-pyrrolo[2,3-d]pyrimidin-4-yl]-amine using an analogous procedure described in Example 1:

| Example Number | Name | m.p. [° C.] | MS-ES⁺: (M + H)⁺ | TLC $R_f$ | HPLC $t_R$ [min] |
|---|---|---|---|---|---|
| 2 | (3-Chloro-4-fluoro-phenyl)-[6-(4-diethylaminomethyl-phenyl)-7H-pyrrolo[2,3-d]pyrimidin-4-yl]-amine | 285-287 | 424 | 0.32[a] | 8.54 |
| 3 | (3-Chloro-4-fluoro-phenyl)-{6-[4-(4-ethyl-piperazin-1-ylmethyl)-phenyl]-7H-pyrrolo[2,3-d]pyrimidin-4-yl}-amine | 266-268 | 465 | 0.42[b] | 7.7 |
| 4 | (3-Chloro-4-fluoro-phenyl)-[6-(4-pyrrolidin-1-ylmethyl-phenyl)-7H-pyrrolo[2,3-d]pyrimidin-4-yl]-amine | 268-270 | 422 | 0.45[b] | 8.4 |
| 5 | (3-Chloro-4-fluoro-phenyl)-{6-[4-(4-methyl-piperazin-1-ylmethyl)-phenyl]-7H-pyrrolo[2,3-d]pyrimidin-4-yl}-amine | 264-266 | 451 | 0.33[b] | 7.5 |
| 6 | (3-Chloro-4-fluoro-phenyl)-[6-(4-piperidin-1-ylmethyl-phenyl)-7H-pyrrolo[2,3-d]pyrimidin-4-yl]-amine | 267-269 | 436 | 0.40[b] | 8.66 |
| 7 | (3-Chloro-4-fluoro-phenyl)-[6-(4-morpholin-4-ylmethyl-phenyl)-7H-pyrrolo[2,3-d]pyrimidin-4-yl]-amine | 298-300 | 438 | 0.21[a] | 8.07 |
| 8 | (3-Chloro-4-fluoro-phenyl)-{6-[4-(3,5-dimethyl-piperazin-1-ylmethyl)-phenyl]-7H-pyrrolo[2,3-d]pyrimidin-4-yl}-amine | 261-263 | 465 | 0.35[b] | 7.53 |
| 8a | (3-Chloro-4-fluoro-phenyl)-(6-{4-[(tetrahydro-pyran-4-ylamino)-methyl]-phenyl}-7H-pyrrolo[2,3-d]pyrimidin-4-yl)-amine | 288-290 | 452 | 0.43[c] | 7.68 |
| 8b | (3-Chloro-4-fluoro-phenyl)-(6-{4-[(2-morpholin-4-yl-ethylamino)-methyl]-phenyl}-7H-pyrrolo[2,3-d]pyrimidin-4-yl)-amine | 224-226 | 481 | 0.3[d] | 7.22 |

-continued

| Example Number | Name | m.p. [° C.] | MS-ES+: (M + H)+ | TLC R$_f$ | HPLC t$_R$ [min] |
|---|---|---|---|---|---|
| 8c | N-{4-[4-(3-Chloro-4-fluoro-phenylamino)-7H-pyrrolo[2,3-d]pyrimidin-6-yl]-benzyl}-N',N'-diethyl-ethane-1,2-diamine | 229-231 | 467 | 0.18$^d$ | 7.41 |
| 8d | (3-Chloro-4-fluoro-phenyl)-{6-[4-(isopropylamino-methyl)-phenyl]-7H-pyrrolo[2,3-d]pyrimidin-4-yl}-amine | 282-284 | 410 | 0.72$^d$ | 8.14 |

$^a$Dichloromethane/ethanol 95:5 + 1% conc. ammonia
$^b$Dichloromethane/ethanol 9:1 + 1% conc. ammonia
$^c$Dichloromethane/ethanol 9:1 + 2% conc. ammonia
$^d$Dichloromethane/ethanol 7:3 + 1% conc. ammonia Example 9

{6-[4-(4-Methyl-piperazin-1-ylmethyl)-phenyl]-7H-pyrro[2,3-d]pyrimidin-4-yl}-((R)-1-phenyl-ethyl)-amine A mixture of 10.8 g (30 mmol) [6-(4-chloromethyl-phenyl)-7H-pyrrolo[2,3-d]pyrimidin-4-yl]-((R)-1-phenyl-ethyl)-amine in 450 ml DMF is treated with 6.8 ml (63 mmol) N-methylpiperazine and 20.7 g (150 mmol) anhydrous potassium carbonate and the mixture heated to 65° C. for 1 hour. The reaction mixture is cooled and the inorganic salts removed by filtration (Hyflo Super Cel®; Fluka, Buchs, Switzerland). The DMF is evaporated under reduced pressure and the residue purified through flash chromatography using first dichloromethane/ethanol 9:1 and then dichloromethane/ethanol 9:1 plus 1% conc. ammonia. Crystallization of the pure fractions from THF (20 ml) and hexanes (80 ml) gives the title compound; m.p. 248-250° C.; MS-ES+: (M+H)+=427.

Step 9.1: 4-[4-((R)-1-Phenyl-ethylamino)-7H-pyrrolo[2,3-d]pyrimidin-6-yl]-benzoic acid ethyl ester 1.8 g (6 mmol) 4-(4-chloro-7H-pyrrolo[2,3-d]pyrimidin-6-yl)-benzoic acid ethyl ester (WO 97/02266) are suspended in 40 ml n-butanol and treated with 1.5 ml (12 mmol) (R)-phenethylamine. The mixture is heated to 145° C. under stirring. After 3 h a clear brown solution is obtained which is treated with a second portion of (R)-phenethylamine (0.75 ml, 6 mmol). After stirring for additional 2 h the reaction mixture is cooled in an ice bath and the title compound filtered and washed with cold n-butanol and ether; m.p. 288-290° C.; MS-ES+: (M+H)+=387.

Step 9.2: {4-[4-((R)-1-Phenyl-ethylamino)-7H-pyrrolo[2,3-d]pyrimidin-6-yl]-phenyl}-methanol 570 mg (15 mmol) lithium aluminum hydride are suspended in 150 ml dry THF at RT. 1.23 g (3 mmol) 4-[4-((R)-1-phenyl-ethylamino)-7H-pyrrolo[2,3-d]pyrimidin-6-yl]-benzoic acid ethyl ester are added and the mixture heated to reflux for 1 h. The mixture is cooled in an ice bath and treated sequentially with water (0.57 ml), 15% sodium hydroxide solution (0.57 ml) and water (1.71 ml). The solid aluminum complex is removed by filtration (Hyflo Super Cel®; Fluka, Buchs, Switzerland), the filtrate dried over sodium sulfate evaporated. The residue is suspended in water, filtered and dried to give the title compound; m.p.>300° C.; R$_f$ (dichloromethane/ethanol 9:1 plus 1% conc. ammonia)=0.43; HPLC t$_R$=8.71 min.

Step 9.3: [6-(4-Chloromethyl-phenyl)-7H-pyrrolo[2,3-d]pyrimidin-4-yl]-((R)-1-phenyl-ethyl)-amine A solution of thionyl chloride (25.7 ml, 0.328 mol) in 180 ml of toluene is cooled to −10° C. Solid {4-[4-((R)-1-phenyl-ethylamino)-7H-pyrrolo[2,3-d]pyrimidin-6-yl]-phenyl}-methanol (11.3 g, 0.0328 mol) is added in 8 portions over a range of 1 h. The temperature is then increased slowly to 0° C. and the mixture stirred for 2 h. The cold reaction mixture is filtered and the solid washed with toluene and ether. The crude product is suspended in water and treated with saturated sodium bicarbonate solution until the mixture turns basic. The mixture is stirred well for about 10 min and filtered. The solid is thoroughly washed with water and dried under reduced pressure to give the title compound; m.p.>320° C.; R$_f$ (dichloromethane/ethanol 9:1)=0.46; HPLC t$_R$=10.63 min; MS-ES+: (M+H)+=363.

Examples 10-16g

The following Examples are synthesized from [6-(4-chloromethyl-phenyl)-7H-pyrrolo[2,3-d]pyrimidin-4-yl]-((R)-1-phenyl-ethyl)-amine using an analogous procedure described in Example 9:

| Example Number | Name | m.p. [° C.] | MS-ES+: (M + H)+ | TLC R$_f$ | HPLC t$_R$ [min] |
|---|---|---|---|---|---|
| 10 | [6-(4-Diethylaminomethyl-phenyl)-7H-pyrrolo[2,3-d]pyrimidin-4-yl]-((R)-1-phenyl-ethyl)-amine | 246-248 | 400 | 0.5$^a$ | 7.96 |
| 11 | {6-[4-(4-Ethyl-piperazin-1-ylmethyl)-phenyl]-7H-pyrrolo[2,3-d]pyrimidin-4-yl}-((R)-1-phenyl-ethyl)-amine | 245-247 | 441 | 0.38$^a$ | 7.14 |

-continued

| Example Number | Name | m.p. [° C.] | MS-ES⁺: (M + H)⁺ | TLC $R_f$ | HPLC $t_R$ [min] |
|---|---|---|---|---|---|
| 12 | ((R)-1-Phenyl-ethyl)-[6-(4-pyrrolidin-1-ylmethyl-phenyl)-7H-pyrrolo[2,3-d]pyrimidin-4-yl]-amine | 254-256 | 398 | 0.5[a] | 7.91 |
| 13 | [6-(4-Dimethylaminomethyl-phenyl)-7H-pyrrolo[2,3-d]pyrimidin-4-yl]-((R)-1-phenyl-ethyl)-amine | 241-243 | 427 | 0.39[a] | 6.35 |
| 14 | ((R)-1-Phenyl-ethyl)-[6-(4-piperidin-1-ylmethyl-phenyl)-7H-pyrrolo[2,3-d]pyrimidin-4-yl]-amine | 246-248 | 412 | 0.53[a] | 8.1 |
| 15 | [6-(4-Morpholin-4-ylmethyl-phenyl)-7H-pyrrolo[2,3-d]pyrimidin-4-yl]-((R)-1-phenyl-ethyl)-amine | 263-265 | 414 | 0.6[a] | 7.5 |
| 16 | {6-[4-(3,5-Dimethyl-piperazin-1-ylmethyl)-phenyl]-7H-pyrrolo[2,3-d]pyrimidin-4-yl}-((R)-1-phenyl-ethyl)-amine | 208-210 | 441 | 0.3[a] | 7.16 |
| 16a | (6-{4-[(2-Morpholin-4-yl-ethylamino)-methyl]-phenyl}-7H-pyrrolo[2,3-d]pyrimidin-4-yl)-((R)-1-phenyl-ethyl)-amine | 222-224 | 457 | 0.46[b] | 6.66 |
| 16b | ((R)-1-Phenyl-ethyl)-(6-{4-[(tetrahydro-pyran-4-ylamino)-methyl]-phenyl}-7H-pyrrolo[2,3-d]pyrimidin-4-yl)-amine | 253-255 | 428 | 0.42[c] | 7.18 |
| 16c | N,N-Diethyl-N'-{4-[4-((R)-1-phenyl-ethylamino)-7H-pyrrolo[2,3-d]pyrimidin-6-yl]-benzyl}-ethane-1,2-diamine | 145-150 | 443 | 0.55[b] | 6.73 |
| 16d | {6-[4-(tert-Butylamino-methyl)-phenyl]-7H-pyrrolo[2,3-d]pyrimidin-4-yl}-((R)-1-phenyl-ethyl)-amine | >300 | 400 | 0.53[c] | 7.68 |
| 16e | {6-[4-(Isopropylamino-methyl)-phenyl]-7H-pyrrolo[2,3-d]pyrimidin-4-yl}-((R)-1-phenyl-ethyl)-amine | 266-268 | 386 | 0.5[c] | 7.66 |
| 16f | [6-(4-Ethylaminomethyl-phenyl)-7H-pyrrolo[2,3-d]pyrimidin-4-yl]-((R)-1-phenyl-ethyl)-amine | 236-238 | 372 | 0.33[c] | 7.41 |
| 16g | [6-(4-Methylaminomethyl-phenyl)-7H-pyrrolo[2,3-d]pyrimidin-4-yl]-((R)-1-phenyl-ethyl)-amine | 234-236 | 358 | 0.1[c] | 7.27 |

[a]Dichloromethane/ethanol 9:1 + 1% conc. ammonia
[b]Dichloromethane/ethanol 7:3 + 2% conc. ammonia
[c]Dichloromethane/ethanol 9:1 + 2% conc. ammonia Example 17

(4-Benzyloxy-phenyl)-[6-(4-dimethylaminomethyl-phenyl)-7H-pyrrolo[2,3-d]pyrimidin-4-yl]-amine A mixture of 220 mg (0.5 mmol) crude (4-benzyloxy-phenyl)[6-(4-chloromethyl-phenyl)-7H-pyrrolo[2,3-d]pyrimidin-4-yl]-amine in 15 ml absolute ethanol is treated with 0.8 ml (5 mmol) of a 33% solution of dimethylamine in ethanol (Fluka, Buchs, Switzerland) and then heated under reflux for 1 h. The resulting solution is cooled and the solvent evaporated. The residue is dissolved in a mixture of dichloromethane and ethanol (95:5), washed with water, dried over sodium sulfate and the solvent evaporated. The solid material is then suspended in ether stirred for 5 min and filtered. Purification of the crude material through flash chromatography using dichloromethane/ethanol 9:1 plus 1% conc. ammonia gives the title compound; m.p. 272-274° C.; MS-ES⁺: (M+H)⁺=450.

Step 17.1 (4-Benzyloxy-phenyl)-[6-(4-chloromethyl-phenyl)-7H-pyrrolo[2,3-d]pydmidin-4-yl]-amine This material is prepared in an analogous procedure as described in steps 1.1 to 1.3; m.p.>300° C.; HPLC $t_R$=12.19 min; MS-ES⁺: (M+H)⁺=441.

Examples 18-24

The following Examples are synthesized from (4-benzyloxy-phenyl)-[6-(4-chloromethyl-phenyl)-7H-pyrrolo[2,3-d]pyrimidin-4-yl]-amine using an analogous procedure described in Example 17:

| Example Number | Name | m.p. [° C.] | MS-ES+: (M + H)+ | TLC R_f | HPLC t_R [min] |
|---|---|---|---|---|---|
| 18 | (4-Benzyloxy-phenyl)-{6-[4-(4-methyl-piperazin-1-ylmethyl)-phenyl]-7H-pyrrolo[2,3-d]pyrimidin-4-yl}-amine | 256-258 | 505 | 0.28[a] | 8.37 |
| 19 | (4-Benzyloxy-phenyl)-[6-(4-piperidin-1-ylmethyl-phenyl)-7H-pyrrolo[2,3-d]pyrimidin-4-yl]-amine | 256-258 | 490 | 0.5[b] | 9.4 |
| 20 | (4-Benzyloxy-phenyl)-[6-(4-morpholin-4-ylmethyl-phenyl)-7H-pyrrolo[2,3-d]pyrimidin-4-yl]-amine | 272-274 | 492 | 0.25[b] | 9.03 |
| 21 | (4-Benzyloxy-phenyl)-[6-(4-diethylaminomethyl-phenyl)-7H-pyrrolo[2,3-d]pyrimidin-4-yl]-amine | 271-273 | 478 | 0.15[a] | 9.30 |
| 22 | (4-Benzyloxy-phenyl)-{6-[4-(4-ethyl-piperazin-1-ylmethyl)-phenyl]-7H-pyrrolo[2,3-d]pyrimidin-4-yl}-amine | 256-258 | 519 | 0.6[b] | 8.37 |
| 23 | (4-Benzyloxy-phenyl)-[6-(4-pyrrolidin-1-ylmethyl-phenyl)-7H-pyrrolo[2,3-d]pyrimidin-4-yl]-amine | 265-267 | 476 | 0.44[b] | 9.23 |
| 24 | (4-Benzyloxy-phenyl)-{6-[4-(3,5-dimethyl-piperazin-1-ylmethyl)-phenyl]-7H-pyrrolo[2,3-d]pyrimidin-4-yl}-amine | 269-271 | 519 | 0.3[b] | 8.32 |

[a]Dichloromethane/ethanol 95:5 + 1% conc. ammonia
[b]Dichloromethane/ethanol 9:1 + 1% conc. ammonia

Example 25

[6-(3-Dimethylaminomethyl-phenyl)-7H-pyrrolo[2,3-d]pyrimidin-4-yl]-((R-1-phenyl-ethyl)-amine A mixture of 240 mg (0.5 mmol) crude [6-(3-chloromethyl-phenyl)-7H-pyrrolo[2,3-d]pyrimidin-4-yl]-((R)-1-phenyl-ethyl)-amine in 15 ml ethanol is treated with 0.8 ml (5 mmol) of a 33% solution of dimethylamine in ethanol (Fluka, Buchs, Switzerland) and then heated under reflux for 1 h. The clear solution is cooled and the solvent evaporated. The residue is purified with flash chromatography using dichloromethane/ethanol 95:5 and then dichloromethane/ethanol 9:1 plus 1% conc. ammonia to give the title compound; m.p. 108-110° C.; MS-ES+: (M+H)+=372.

Step 25.1: {3-[4-((R)-1-Phenyl-ethylamino)-7H-pyrrolo[2,3-d]pyrimidin-6-yl]-phenyl}methanol This material is prepared in an analogous procedure as described in steps 9.1 to 9.2; m.p. 217-219° C.; MS-ES+: (M+H)+=345.

Step 25.2: [6-(3-Chloromethyl-phenyl)-7H-pyrrolo[2,3-d]pyrimidin-4-yl]-((R)-1-phenyl-ethyl)-amine A mixture of 688 mg (2 mmol) {3-[4-((R)-1-phenyl-ethylamino)-7H-pyrrolo[2,3-d]pyrimidin-6-yl]-phenyl}-methanol and 578 mg (2.2 mmol) triphenylphosphine in 60 ml dichloromethane is treated at 0° C. with 293 mg (2.2 mmol) N-chlorosuccinimide. After stirring 1 h at 0° C. all the material has gone into solution. The solvent is evaporated and the title compound purified with flash chromatography using dichloromethane/ethanol 95:5 (the title compound is contaminated with a small amount of triphenylphosphine oxide); R_f (dichloromethane/ethanol 95:5)=0.35; MS-ES+: (M+H)+=363.

Examples 26-32

The following Examples are synthesized from [6-(3-chloromethyl-phenyl)-7H-pyrrolo[2,3-d]pyrimidin-4-yl]-((R)-1-phenyl-ethyl)-amine using an analogous procedure as described in Example 25:

| Example Number | Name | m.p. [° C.] | MS-ES+: (M + H)+ | TLC R_f | HPLC t_R [min] |
|---|---|---|---|---|---|
| 26 | [6-(3-Diethylaminomethyl-phenyl)-7H-pyrrolo[2,3-d]pyrimidin-4-yl]-((R)-1-phenyl-ethyl)-amine | 110-113 | 400 | 0.6[a] | 8.15 |
| 27 | {6-[3-(4-Ethyl-piperazin-1-ylmethyl)-phenyl]-7H-pyrrolo[2,3-d]pyrimidin-4-yl}-((R)-1-phenyl-ethyl)-amine | 128-130 | 441 | 0.34[b] | 7.3 |

-continued

| Example Number | Name | m.p. [° C.] | MS-ES+: (M + H)+ | TLC $R_f$ | HPLC $t_R$ [min] |
|---|---|---|---|---|---|
| 28 | ((R)-1-Phenyl-ethyl)-[6-(3-pyrrolidin-1-ylmethyl-phenyl)-7H-pyrrolo[2,3-d]pyrimidin-4-yl]-amine | 90-92 | 398 | 0.50[b] | 7.97 |
| 29 | {6-[3-(4-Methyl-piperazin-1-ylmethyl)-phenyl]-7H-pyrrolo[2,3-d]pyrimidin-4-yl}-((R)-1-phenyl-ethyl)-amine | 112-115 | 427 | 0.27[b] | 7.25 |
| 30 | ((R)-1-Phenyl-ethyl)-[6-(3-piperidin-1-ylmethyl-phenyl)-7H-pyrrolo[2,3-d]pyrimidin-4-yl]-amine | 108-110 | 412 | 0.6[b] | 8.19 |
| 31 | [6-(3-Morpholin-4-ylmethyl-phenyl)-7H-pyrrolo[2,3-d]pyrimidin-4-yl]-((R)-1-phenyl-ethyl)-amine | 242-243 | 414 | 0.28[a] | 7.8 |
| 32 | {6-[3-(3,5-Dimethyl-piperazin-1-ylmethyl)-phenyl]-7H-pyrrolo[2,3-d]pyrimidin-4-yl}-((R)-1-phenyl-ethyl)-amine | 128-130 | 441 | 0.3[b] | 7.18 |

[a]Dichloromethane/ethanol 95:5 + 1% conc. ammonia
[b]Dichloromethane/ethanol 9:1 + 1% conc. ammonia

Example 33

(3-Chloro-4-fluoro-phenyl)-[6-(3-dimetylaminomethyl-phenyl)-7H-pyrrolo[2,3-d]pyrimidin-4-yl]-amine The compound is synthesized analogously to Example 1 starting with (3-chloro-4-fluoro-phenyl)-[6-(3-chloromethyl-phenyl)-7H-pyrrolo[2,3-d]pyrimidin-4-yl]-amine; m.p. 218-220° C.; MS-ES+: (M+H)+=396.

Step 33.1: (3-Chloro-4-fluoro-phenyl)-[6-(3-chloromethyl-phenyl)-7H-pyrrolo[2,3-d]pyrimidin-4-yl]-amine The title compound is prepared in an analogous procedure as described in steps 1.1 to 1.3; $R_f$ (dichloromethane/ethanol 95:5 plus 1% conc. ammonia)=0.45; MS-ES+: (M+H)+=387.

Examples 34-39

The following Examples are synthesized from (3-chloro-4-fluorophenyl)-[6-(3-chloromethyl-phenyl)-7H-pyrrolo[2,3-d]pyrimidin-4-yl]-amine using an analogous procedure as described in Example 33:

| Example Number | Name | m.p. [° C.] | MS-ES+: (M + H)+ | TLC $R_f$ | HPLC $t_R$ [min] |
|---|---|---|---|---|---|
| 34 | (3-Chloro-4-fluoro-phenyl)-[6-(3-diethylaminomethyl-phenyl)-7H-pyrrolo[2,3-d]pyrimidin-4-yl]-amine | 210-212 | 424 | 0.32[a] | 8.76 |
| 35 | (3-Chloro-4-fluoro-phenyl)-{6-[3-(4-ethyl-piperazin-1-ylmethyl)-phenyl]-7H-pyrrolo[2,3-d]pyrimidin-4-yl}-amine | 238-240 | 465 | 0.4[b] | 7.7 |
| 36 | (3-Chloro-4-fluoro-phenyl)-[6-(3-pyrrolidin-1-ylmethyl-phenyl)-7H-pyrrolo[2,3-d]pyrimidin-4-yl]-amine | 238-240 | 422 | 0.45[b] | 8.44 |
| 37 | (3-Chloro-4-fluoro-phenyl)-{6-[3-(4-methyl-piperazin-1-ylmethyl)-phenyl]-7H-pyrrolo[2,3-d]pyrimidin-4-yl}-amine | 221-223 | 451 | 0.33[b] | 7.6 |
| 38 | (3-Chloro-4-fluoro-phenyl)-[6-(3-piperidin-1-ylmethyl-phenyl)-7H-pyrrolo[2,3-d]pyrimidin-4-yl]-amine | 233-235 | 436 | 0.45[b] | 8.75 |

-continued

| Example Number | Name | m.p. [° C.] | MS-ES+: (M + H)+ | TLC $R_f$ | HPLC $t_R$ [min] |
|---|---|---|---|---|---|
| 39 | (3-Chloro-4-fluoro-phenyl)-[6-(3-morpholin-4-ylmethyl-phenyl)-7H-pyrrolo[2,3-d]pyrimidin-4-yl]-amine | 290-292 | 438 | 0.21[a] | 8.15 |

[a]Dichloromethane/ethanol 95:5 + 1% conc. ammonia
[b]Dichloromethane/ethanol 9:1 + 1% conc. ammonia Example 40

N-{4-[4-((R)-1-Phenyl-ethylamino)-7H-pyrrolo[2,3-d]pyrimidin-6-yl]-benzyl}-2-piperidin-1-yl-acetamide A mixture of 80 mg (0.19 mmol) 2-chloro-N-{4-[4-((R)-1-phenyl-ethylamino)-7H-pyrrolo[2,3d]pyrimidin-6-yl]-benzyl}acetamide in 1.5 ml n-butanol is treated with 47 µl (0.48 mmol) piperidine and then heated to 100° C. for 2 h. The clear solution is cooled and the solvent evaporated. The residue is purified with flash chromatography using a mixture of ethyl acetate/methanol with increasing concentrations of methanol starting with 100:2.5 and ending with 10:1. The title compound is obtained as a colorless powder; m.p. 194-196° C.; MS-ES+: (M+H)+=469.

Step 40.1: 2-Amino-5-(4-cyano-phenyl)-1H-pyrrole-3-carboxylic acid ethyl ester

A mixture of 42.53 g (0.255 mol) carbamimidoyl-acetic acid ethyl ester hydrochloride in 70 ml absolute ethanol is treated at 0 to 5° C. with 95.3 ml of a 21% sodium ethoxide solution in ethanol (0.255 mol) and stirred 5 min at 0 to 5° C. 4-Bromoacetyl-benzonitrile (28.6 g, 0.128 mol) is then added in portions over 20 min at 0 to 5° C. Stirring is continued at this temperature for 5 min then the ice bath is removed and the yellow suspension is stirred over night at RT. The solid is filtered off, washed with ethanol and ether and re-suspended in 450 ml actonitrile. The mixture is heated for 5 min under reflux, filtered while still hot and then cooled in an ice bath. The title compound is collected by succion and dried. Flash chromatography (dichtoromethane/ethyl acetate mixture) of the mother liquors gives an additional crop of the title compound as a yellow solid; m.p. 228-229° C.; MS-ES+: (M+H)+ =254.

Step 40.2: 4-(4-Hydroxy-7H-pyrrolo[2,3-d]pyrimidin-6-yl)-benzonitrile

A mixture of 36.6 g (0.143 mol) 2-amino-5-(4-cyano-phenyl)-1H-pyrrole-3-carboxylic acid ethyl ester, 140 ml DMF, 305 ml formamide and 14.6 ml 85% formic acid is heated for 16 h at 150° C. The resulting yellow suspension is cooled to 10° C. and filtered. The solid is washed with methanol (120 ml) and ether (150 ml) and dried. The title compound is obtained as yellowish crystals; m.p.>410° C.; MS-ES+: (M+H)+=254.

Step 40.3: 4-(4-Chloro-7H-pyrrolo[2,3-d]pyrimidin-4-6-yl)-benzonitrile 4-(4-Hydroxy-7H-pyrrolo[2,3-d]pyrimidin-6-yl)-benzonitrile (2,36 9. 0.01 mol) are suspended in 40 ml acetonitril and 4.99 ml (0.02 mol) 4 N hydrochloric acid solution in dioxane. After addition of 3.66 ml (0.04 mol) phosphorus oxichloride the mixture is heated under reflux for 3 days. The solid is filtered off and the mother liquor evaporated. The residue and the solid are dissolved in 30 ml DMF at 60° C. and 25 ml of a conc. sodium bicarbonate solution and 25 ml water are added and the resulting suspension cooled, filtered and the solid washed with water. The title compound is dried at 100° C. for 6 h under reduced pressure; m.p. 296-297° C.; HPLC $t_R$=11.59 min.

Step 40.4: 4-[4-((R)-1-Phenyl-ethylamino)-7H-pyrrolo[2,3-d]pyrimidin-6-yl]-benzonitrile A mixture of 1.27 g (5 mmol) 4-(4-chloro-7H-pyrrolo[2,3-d]pyrimidin-6-yl)-benzonitrile, 1.4 ml (10 mol) triethylamine and 0.955 ml (7.5 mmol) R(+)-1-phenyl-ethylamine in 25 ml dioxane is heated under reflux for 24 h. A second portion of R(+)-1-phenyl-ethylamine (0.32 ml, 2.5 mmol) is added and heating is continued for 24 h. After addition of a third portion of R(+)-1-phenyl-ethylamine (0.32 ml, 2.5 mmol) and additional 24 h the reaction mixture is cooled to 10° C. and the title compound filtered off and washed with dioxane. From the mother liquor a second crop is obtained after concentration of the solution; m.p. 333-336° C.; MS-ES+: (M+H)+=340.

Step 40.5: [6-(4-Aminomethyl-phenyl)-7H-pyrrolo[2,3-d]pyrimidin-4-yl]-((R)-1-phenyl-ethyl)-amine Raney-Nickel (0.1 9) catalyzed hydrogenation of 0.206 g (0.6 mmol) 4-[4-((R)-1-phenyl-ethylamino)-7H-pyrrolo[2,3-d]pyrimidin-6-yl]-benzonitrile in a mixture of 5% ammonia in methanol (20 ml) and THF (4 ml) for 6 h at atmospheric pressure followed by filtration and evaporation of the solvent gives the title compound; m.p. 253-256° C.; MS-ES+: (M+H)+=344.

Step 40.6: 2-Chloro-N-{4-[4-((R)-1-phenyl-ethylamino)-7H-pyrrolo[2,3-d]pyrimidin-6-yl]-benzyl}-acetamide A mixture of 0.21 g (0.6 mmol)[6-(4-aminomethyl-phenyl)-7H-pyrrolo[2,3-d]pyrimidin-4-yl]-((R)-1-phenyl-ethyl)-amine and 94 µl (0.67 mmol) triethylamine in 5 ml dry THF is treated dropwise with a solution of chloro-acetyl chloride (51 µl, 0.64 mmol) in 0.5 ml of dry THF at RT. After stirring for 30 min small amounts of insoluble material is removed by filtration and the filtrate is evaporated. The residue is purified by flash chromatography using ethyl acetate/methanol 100:2 to 100:4 as eluent. The title compound is obtained as light brown solid HPLC $t_R$=9.36 min; MS-ES+: (M+H)+=420.

Examples 41-45

The following Examples are synthesized from 2-chloro-N-{4-[4-((R)-1-phenyl-ethylamino)-7H-pyrrolo[2,3-d]pyrimidin-6-yl]-benzyl}-acetamide using an analogous procedure as described in Example 40:

| Example Number | Name | m.p. [° C.] | MS-ES⁺: (M + H)⁺ | TLC $R_f$ | HPLC $t_R$ [min] |
|---|---|---|---|---|---|
| 41 | N-{4-[4-((R)-1-Phenyl-ethylamino)-7H-pyrrolo[2,3-d]pyrimidin-6-yl]-benzyl}-2-pyrrolidin-1-yl-acetamide | 196-198 | 455 | 0.25[a] | 7.92 |
| 42 | 2-Morpholin-4-yl-N-{4-[4-((R)-1-phenyl-ethylamino)-7H-pyrrolo[2,3-d]pyrimidin-6-yl]-benzyl}-acetamide | 199-202 | 471 | 0.28[a] | 7.78 |
| 43 | 2-(4-Methyl-piperazin-1-yl)-N-{4-[4-((R)-1-phenyl-ethylamino)-7H-pyrrolo[2,3-d]pyrimidin-6-yl]-benzyl}-acetamide | 150-152 | 484 | 0.29[b] | 7.45 |
| 44 | 2-Dimethylamino-N-{4-[4-((R)-1-phenyl-ethylamino)-7H-pyrrolo[2,3-d]pyrimidin-6-yl]-benzyl}-acetamide | 263-266 | 429 | 0.21[a] | 7.64 |
| 45 | 2-(4-Ethyl-piperazin-1-yl)-N-{4-[4-((R)-1-phenyl-ethylamino)-7H-pyrrolo[2,3-d]pyrimidin-6-yl]-benzyl}-acetamide | 121-124 | 498 | 0.26[b] | 7.66 |

[a]dichloromethane/methanol 9:1
[b]dichloromethane/methanol/conc. ammonia 90:10:1

Example 46

N-{4-[4-(3-Chloro-4-fluoro-phenylamino)-7H-pyrrolo[2,3-d]pyrimidin-6-yl]-benzyl}-2-dimethylamino-acetamide 2-Chloro-N-{4-[4-(3-chloro-4-fluoro-phenylamino)-7H-pyrrolo[2,3-d]pyrimidin-6-yl]-benzyl}-acetamide (100 mg, 0.225 mmol) in 2 ml n-butanol and 0.12 ml (0.67 mmol) 5.6 N dimethylamine in ethanol (Fluka, Buchs, Switzerland) is stirred and heated to 100° C. for 6 h. The mixture is cooled, filtered and the solid re-suspended in 3 ml hot ethanol. After cooling the title compound is collected by filtration, washed with ethanol and dried; m.p. 278-282; $R_f$ (ethyl acetate/methanol 8:2)=0.14; HPLC $t_R$=8.04 min; MS-ES⁺: (M+H)⁺=453.

Step 46.1: 2-Chloro-N-{4-[4-(3-chloro-4-fluoro-phenylamino)-7H-pyrrolo[2,3-d]pyrimidin-6-yl]-benzyl}-acetamide This compound is synthesized using an analogous sequence as described for 2-chloro-N-{4-[4-((R)-1-phenyl-ethylamino)-7H-pyrrolo[2,3-d]pyrimidin-6-yl]-benzyl}-acetamide (steps 40.4 to 40.6); m.p. 320-325° C.; $R_f$ (dichloromethane/methanol/conc. ammonia 90:10:1)=0.39; MS-ES⁺: (M+H)⁺=444.

Examples 47-50

The following Examples are synthesized from 2-chloro-N-{4-[4-(3-chloro-4-fluoro-phenylamino)-7H-pyrrolo[2,3-d]pyrimidin-6-yl]-benzyl}-acetamide using an analogous procedure as described in Example 46:

| Example Number | Name | m.p. [° C.] | MS-ES⁺: (M + H)⁺ | TLC $R_f$ | HPLC $t_R$ [min] |
|---|---|---|---|---|---|
| 47 | N-{4-[4-(3-Chloro-4-fluoro-phenylamino)-7H-pyrrolo[2,3-d]pyrimidin-6-yl]-benzyl}-2-(4-ethyl-piperazin-1-yl)-acetamide | 245-247 | 522 | 0.53[a] | 8.04 |
| 48 | N-{4-[4-(3-Chloro-4-fluoro-phenylamino)-7H-pyrrolo[2,3-d]pyrimidin-6-yl]-benzyl}-2-morpholin-4-yl-acetamide | 272-275 | 495 | 0.48[b] | 8.19 |
| 49 | N-{4-[4-(3-Chloro-4-fluoro-phenylamino)-7H-pyrrolo[2,3-d]pyrimidin-6-yl]-benzyl}-2-piperidin-1-yl-acetamide | 229-232 | 495 | 0.48[a] | 8.52 |
| 50 | N-{4-[4-(3-Chloro-4-fluoro-phenylamino)-7H-pyrrolo[2,3-d]pyrimidin-6-yl]-benzyl}-2-(4-methyl-piperazin-1-yl)-acetamide | 246-249 | 508 | 0.61[a] | 7.93 |

[a]dichloromethane/methanol/conc. ammonia 40:10:1
[b]ethyl acetate/methanol 8:2

Example 51

N-{4-[4-(4-Benzyloxy-phendamine)-7H-pyrrolo[2,3-d]pyrimidin-6-yl]-benzyl}-2-dimethylamino-acetamide N-{4-[4-(4-Benzyloxy-phenylamino)-7H-pyrrolo[2,3-d]pyrimidin-6-yl]-benzyl}-2-chloro-acetamide (0.2 g, 0.4 mmol) in 3 ml n-butanol and 0.215 ml (1.2 mmol) 5.6 N dimethylamine in ethanol (Fluka, Buchs, Switzerland) is stirred and heated to 100° C. for 6 h. After addition of a second portion of dimethylamine solution (0.3 ml, 1.68 mmol) the mixture is heated for 6 more hours. The mixture is then cooled, filtered and the solid re-suspended in 3 ml warm dichloromethane/methanol 2:1. After cooling the title compound is collected by filtration and purified further with flash chromatography using a gradient of dichloromethane/methanol 100:2.5 to 10:1; m.p. 233-235; MS-ES$^+$: (M+H)$^+$=507.

Step 51.1: N-{4-[4-(4-Benzyloxy-phenylamino)-7H-pyrrolo[2,3-d]pyrimidin-6-yl]-benzyl}-2-chloro-acetamide This compound is synthesized using an analogous sequence as described for 2-chloro-N-{4-[4-((R)-1-phenyl-ethylamino)-7H-pyrrolo[2,3-d]pyrimidin-6-yl]-benzyl}-acetamide (steps 40.4 to 40.6); R$_f$(dichloromethane/methanol/conc. ammonia 90:10:1)=0.40; MS-ES$^+$: (M+H)$^+$=498.

Examples 52-53

The following Examples are synthesized from N-{4-[4-(4-benzyloxy-phenylamino)-7H-pyrrolo[2,3-d]pyrimidin-6-yl]-benzyl}-2-chloro-acetamide using an analogous procedure as described in Example 51:

Example 54

N-{4-[4-((R)-1-Phenyl-ethylamino)-7H-pyrrolo[2-3-d]pyrimidin-6-yl]-benzyl}-3-piperidin-1-yl-propionamide Under an atmosphere of nitrogen a mixture of 0.0865 g (0.55 mmol) 3-piperidin-1-yl-propionic acid and 0.117 ml (0.68 mmol) N,N-diisopropylethylamine in DMF (5 ml) is treated at RT and over a period of 5 min with a solution of 0.163 g (0.56 mmol) O-(1,2-dihydro-2-oxo-1-pyridyl)-N,N,N',N'-tetramethyluronium-tetrafluroborate (TPTU, Fluka, Buchs, Switzerland) in 2 ml DMF. After stirring for 5 min the resulting solution is added slowly (1.5. h) at RT to 0.172 g (0.5 mmol) [6-(4-aminomethyl-phenyl)-7H-pyrrolo[2,3-d]pyrimidin-4-yl]-((R)-1-phenyl-ethyl)-amine (step 40.5) in 3 ml DMF. The reaction mixture is allowed to stand over night after which the DMF is evaporated under reduced pressure. The residue is purified by flash chromatography using gradients of first dichloromethane/methanol 100:2.5 to 10:1 and then mixtures of dichloromethane/methanol/conc. ammonia 90:10:0.5 to 40:10:1. The title compound is obtained as yellowish solid; m.p. 140° C.; MS-ES$^+$: (M+H)$^+$=483. As a second product of this reaction N-{4-[4-((R)-1-phenyt-ethylamino)-7H-pyrrolo[2,3-d]pyrimidin-6-yl]-benzyl}-acrylamide is obtained; m.p. 249-250° C.; MS-ES$^+$: (M+H)$^+$=398.

Examples 55-57

The following Examples are synthesized from [6-(4-aminomethyl-phenyl)-7H-pyrrolo[2,3-d]pyrimidin-4-yl]-((R)-1-phenylethyl)-amine (step 40.5) using an analogous procedure as described in Example 54:

| Example Number | Name | m.p. [° C.] | MS-ES$^+$: (M + H)$^+$ | TLC R$_f$ | HPLC t$_R$ [min] |
|---|---|---|---|---|---|
| 52 | N-{4-[4-(4-Benzyloxy-phenylamino)-7H-pyrrolo[2,3-d]pyrimidin-6-yl]-benzyl}-2-(4-methyl-piperazin-1-yl)-acetamide | 232-234 | 562 | 0.18[a] | 8.69 |
| 53 | N-{4-[4-(4-Benzyloxy-phenylamino)-7H-pyrrolo[2,3-d]pyrimidin-6-yl]-benzyl}-2-piperidin-1-yl-acetamide | 246-248 | 547 | 0.42[b] | 9.31 |

[a]dichloromethane/methanol/conc. ammonia 90:10:1
[b]dichloromethane/methanol 85:15

| Example Number | Name | m.p. [° C.] | MS-ES⁺: (M + H)⁺ | TLC $R_f$ | HPLC $t_R$ [min] |
|---|---|---|---|---|---|
| 55 | 3-Diethylamino-N-{4-[4-((R)-1-phenyl-ethylamino)-7H-pyrrolo[2,3-d]pyrimidin-6-yl]-benzyl}-propionamide | 175-177 | 471 | 0.19[a] | 8.11 |
| 56 | 4-Dimethylamino-N-{4-[4-((R)-1-phenyl-ethylamino)-7H-pyrrolo[2,3-d]pyrimidin-6-yl]-benzyl}-butyramide | 195-203 | 457 | 0.04[a] | 7.76 |
| 57 | Pyridine-2-carboxylic acid 4-[4-((R)-1-phenyl-ethylamino)-7H-pyrrolo[2,3-d]pyrimidin-6-yl]-benzylamide | 221-223 | 449 | 0.51[a] | 10.16 |

[a]dichloromethane/methanol/conc. ammonia 90:10:1

Example 58

N-{4-[4-(3-Chloro-4-fluoro-phenylamino)-7H-pyrrolo[2,3-d]pyrimidin-6-yl]-benzyl}-3-diethylamino-propionamide The title compound is synthesized from [6-(4-aminomethyl-phenyl)-7H-pyrrolo[2,3-d]pyrimidin-4-yl]-(3-chloro-4-fluoro-phenyl)-amine using an analogous procedure as described in Example 54. In this case activation of the carboxylic acid is done with (benzotriazole-1-yloxy)-tris-(dimethylamino)-phosphonium-hexafluoroborate (BOP, Fluka, Buchs, Switzerland) and N-methylmorpholin; m.p. 229-232; HPLC $t_R$=8.52 min; MS-ES⁺: (M+H)⁺=495.

Step 58.1: [6-(4-Aminomethyl-phenyl)-7H-pyrrolo[2,3-d]pyrimidin-4-yl]-(3-chloro-4-fluoro-phenyl)-amine The title compound is synthesized using an analogous procedure as described in steps 40.4 to 40.5; m.p. 350-351; MS-ES⁺: (M+H)³⁰=368.

Examples 59-61

The following Examples are synthesized from [6-(4-aminomethyl-phenyl)-7H-pyrrolo[2,3-d]pyrimidin-4-yl]-(3-chloro-4-fluoro-phenyl)-amine (step 58.1) using an analogous procedure as described in Example 58:

Example 62

2-Dimethylamino-N-{3-[4-((R)-1-phenyl-ethylamino)-7H-pyrrolo[2,3-d]pyrimidin-6-yl]-benzyl}-acetamide A mixture of 210 mg (0.5 mmol) 2-chloro-N-{3-[4-((R)-1-phenyl-ethylamino)-7H-pyrrolo[2,3-d]pyrimidin-6-yl]-benzyl}-acetamide in 3 ml dry dioxane is treated with 268 µl (1.5 mmol) of a 5.6 N dimethylamine solution in ethanol (Fluka, Buchs, Switzerland) and then heated to 100° C. for 6 h. The clear yellow solution is cooled and the solvent evaporated. The residue is purified by flash chromatography using a mixture of dichloromethane/methanol with gradually increasing concentrations of methanol starting with 100:2.5 and ending with 100:5 and then switching to dichloromethane/methanol/conc. ammonia starting with 100:5:0.25 and ending with 100:10:0.5. The title compound is obtained as a colorless foam; $R_f$(dichloromethane/methanol/conc. ammonia 90:10:1)=0.41; MS-ES⁺: (M+H)⁺=429.

Step 62.1: 2-Chloro-N-{3-[4-((R)-1-phenyl-ethylamino)-7H-pyrrolo[2,3-d]pyrimidin-6-yl]-benzyl}acetamide The title compound is synthesized using an analogous procedure as described in steps 40.1 to 40.6; m.p. 300-310 (decomposition); $R_f$ (dichloromethane/methanol/conc. ammonia 90:10:1)=0.54; MS-ES⁺: (M+H)⁺=420.

| Example Number | Name | m.p. [° C.] | MS-ES⁺: (M + H)⁺ | TLC $R_f$ | HPLC $t_R$ [min] |
|---|---|---|---|---|---|
| 59 | Pyridine-2-carboxylic acid 4-[4-(3-chloro-4-fluoro-phenylamino)-7H-pyrrolo[2,3-d]pyrimidin-6-yl]-benzylamide | 340-342 | 473 | — | 10.62 |
| 60 | N-{4-[4-(3-Chloro-4-fluoro-phenylamino)-7H-pyrrolo[2,3-d]pyrimidin-6-yl]-benzyl}-4-dimethylamino-butyramide | 272-273 | 481 | 0.31[a] | 8.15 |
| 61 | N-{4-[4-(3-Chloro-4-fluoro-phenylamino)-7H-pyrrolo[2,3-d]pyrimidin-6-yl]-benzyl}-3-piperidin-1-yl-propionamide | 230-235 | 507 | 0.76[a] | 8.66 |

[a]dichloromethane/methanol/conc. ammonia 40:10:1

Example 63

2-(4-Methyl-piperazin-1-yl)-N-{3-[4-((R)-1-phenyl-ethylamino)-7H-pyrrolo[2,3-d]pyrimidin-6-yl]-benzyl}-acetamide The title compound is obtained as a tan resin using an analogous procedure as described in Example 62; $R_f$(dichloromethanel/methanol/conc. ammonia 90:10:1)=0.20; HPLC $t_R$=7.77 min; MS-ES$^+$: (M+H)$^+$=484.

Example 64

N-{3-[4-(3-Chloro-4-fluoro-phenylamino)-7H-pyrrolo[2,3-d]pyrimidin-6-yl]-benzyl}-2-dimethylamino-acetamide 2-Chloro-N-{3-[4-(3-chloro-4-fluoro-phenylamino)-7H-pyrrolo[2,3-d]pyrimidin-6-yl]-benzyl}-acetamide (120 mg, 0.222 mmol) in 2 ml dioxane and 0.145 ml (0.81 mmol) 5.6 N dimethylamine in ethanol (Fluka, Buchs, Switzerland) is stirred and heated to 100° C. for 4.5 h. The mixture is cooled and the solvent evaporated. The residue is shaken with THF (5 ml), dichloromethane (3 ml), methanol (2 ml) and saturated sodium bicarbonate (2 ml). The two clear layers are separated and the organic phase is treated with 1 g silica gel. The solution containing the silica gel is evaporated and the solid put on top of a flash chromatography column containing 33 g of silica gel. The column is eluted using a mixture of dichloromethane/methanol with gradually increasing concentrations of methanol starting with 100:2.5 and ending with 100:5 and then switching to dichloromethane/methanol/conc. ammonia starting with 100:5:0.25 and ending with 100:10:0.5. The title compound is obtained as colorless crystals; m.p. 272-273° C.: MS-ES$^+$: (M+H)$^+$=453.

Step 64.1: 2-Chloro-N-{3-[4-(3-chloro-4-fluoro-phenylamino)-7H-pyrrolo[2,3-d]pydmidin-6-yl]-benzyl}-acetamide The title compound is synthesized using an analogous procedure as described in steps 40.1 to 40.6; $R_f$ (dichloromethane/methanol/conc. ammonia 90:10:1)=0.47; HPLC $t_R$=9.98 min; MS-ES$^+$: (M+H)$^+$=444.

Examples 65-66

The following Examples are synthesized from 2-chloro-N-{3-[4-(3-chloro-4-fluoro-phenylamino)-7H-pyrrolo[2,3-d]pyrimidin-6-yl]-benzyl}acetamide (step 64.1) using an analogous procedure as described in Example 64:

| Example Number | Name | m.p. [° C.] | MS-ES$^+$: (M + H)$^+$ | TLC[a] $R_f$ | HPLC $t_R$ [min] |
|---|---|---|---|---|---|
| 65 | N-{3-[4-(3-Chloro-4-fluoro-phenylamino)-7H-pyrrolo[2,3-d]pyrimidin-6-yl]-benzyl}-2-(4-methyl-piperazin-1-yl)-acetamide | 214-214 | 508 | 0.21 | 8.08 |
| 66 | N-{3-[4-(3-Chloro-4-fluoro-phenylamino)-7H-pyrrolo[2,3-d]pyrimidin-6-yl]-benzyl}-2-piperidin-1-yl-acetamide | 252-254 | 493 | 0.53 | 8.65 |

[a]Dichloromethane/methanol/conc. ammonia 90:10:1

Examples 67-78

The following Examples are synthesized using an analogous procedure as described in Example 1. However, a modified protocol is applied for the preparation of the intermediates: Instead of reducing the ethyl-ester with lithium aluminum hydride in THF (as described in step 1.2), the 4-hydroxymethyl derivatives are prepared by reduction with diisobutyl-aluminium hydride in a 1:1 mixture of dichloromethane and dioxane at ambient temperature (Examples 67-72 and 76-78). For preparing the intermediates of Examples 73-75, reduction of 4-(4-chloro-7H-pyrrolo[2,3-d]pyrimidin-6-yl)-benzoic acid ethyl ester with diisobutyl-aluminium hydride in THF at ambient temperature yields [4-(4-chloro-7H-pyrrolo[2,3-d]pyrimidin-6-yl)-phenyl]-methanol (see step 108.3). Substitution of the chlorine by 2-methoxy-5-aminophenol as described in step 1.1 then gives 5-[6-(4-hydroxymethyl-phenyl)-7H-pyrrolo[2,3-d]pyrimidin-4-ylamino]-2-methoxy-phenol.

| Example Number | Name | m.p. [° C.] | MS-ES$^+$: (M + H)$^+$ | TLC $R_f$ | HPLC[a] $t_R$ [min] |
|---|---|---|---|---|---|
| 67 | 2-Methyl-5-{6-[3-(4-methyl-piperazin-1-ylmethyl)-phenyl]- | 256-258 | 429 | 0.14[b] | 6.8 |

-continued

| Example Number | Name | m.p. [° C.] | MS-ES⁺: (M + H)⁺ | TLC R_f | HPLC^a t_R [min] |
|---|---|---|---|---|---|
|  | 7H-pyrrolo[2,3-d]pyrimidin-4-ylamino}-phenol |  |  |  |  |
| 68 | 5-[6-(3-Dimethylaminomethyl-phenyl)-7H-pyrrolo[2,3-d]pyrimidin-4-ylamino]-2-methyl-phenol | 258-260 | 374 | 0.21$^b$ | 7.2 |
| 69 | 2-Methoxy-5-{6-[3-(4-methyl-piperazin-1-ylmethyl)-phenyl]-7H-pyrrolo[2,3-d]pyrimidin-4-ylamino}-phenol | 251-252 | 445 | 0.16$^b$ | 6.1 |
| 70 | 5-[6-(3-Dimethylaminomethyl-phenyl)-7H-pyrrolo[2,3-d]pyrimidin-4-ylamino]-2-methoxy-phenol | 250-251 | 390 | 0.17$^b$ | 6.8 |
| 71 | 5-[6-(4-Dimethylaminomethyl-phenyl)-7H-pyrrolo[2,3-d]pyrimidin-4-ylamino]-2-methyl-phenol |  | 374 | 0.31$^b$ | 7.2 |
| 72 | 2-Methyl-5-{6-[4-(4-methyl-piperazin-1-ylmethyl)-phenyl]-7H-pyrrolo[2,3-d]pyrimidin-4-ylamino}-phenol | >300 | 429 |  | 6.9 |
| 73 | 5-[6-(4-Dimethylaminomethyl-phenyl)-7H-pyrrolo[2,3-d]pyrimidin-4-ylamino]-2-methoxy-phenol |  |  |  |  |
| 74 | 2-Methoxy-5-{6-[4-(4-methyl-piperazin-1-ylmethyl)-phenyl]-7H-pyrrolo[2,3-d]pyrimidin-4-ylamino}-phenol |  | 445 | 0.19$^d$ | 6.3 |
| 75 | 2-Methoxy-5-[6-(4-morpholin-4-ylmethyl-phenyl)-7H-pyrrolo[2,3-d]pyrimidin-4-ylamino]-phenol |  |  |  |  |
| 76 | [(R)-1-(4-Chloro-phenyl)-ethyl]-[6-(4-dimethylaminomethyl-phenyl)-7H-pyrrolo[2,3-d]pyrimidin-4-yl]-amine | 273-274 | 406 | 0.32$^b$ | 9.1 |
| 77 | [(R)-1-(4-Chloro-phenyl)-ethyl]-{6-[4-(4-methyl-piperazin-1-ylmethyl)-phenyl]-7H-pyrrolo[2,3-d]pyrimidin-4-yl}-amine | 232-233 | 461 | 0.31$^b$ | 8.6 |
| 78 | [(R)-1-(4-Chloro-phenyl)-ethyl]-[6-(4-morpholin-4-ylmethyl-phenyl)-7H-pyrrolo[2,3-d]pyrimidin-4-yl]-amine |  | 448 | 0.16$^c$ | 9.2 |

$^a$HPLC: Column: (250 × 4.6 mm) packed with reversed-phase material C18-Nucleosil (5 μm mean particle size, with silica gel covalently derivatized with octadecylsilanes, Macherey & Nagel, Düren, Germany). Detection by UV absorption at 215 nm. The retention times (t_R) are given in minutes. Flow rate: 1 ml/min. Gradient: 20% → 100% a) in b) for 13 min + 5 min 100% a). a): Acetonitrile + 0.05% TFA; b): water + 0.05% TFA.
$^b$Dichloromethane/ethanol 4:1 + drop of conc. ammonia
$^c$EtOAc/ethanol 9:1
$^d$THF/methanol 9:1 + drop of conc. Ammonia Example 79

(3-Chloro-phenyl)-[6-(4-dimethylaminomethyl-phenyl)-7H-pyrrolo[2,3-d]pyrimidin-4-yl]-amine hydrochloride Lithium aluminum hydride (72 mg, 1.9 mmol) is suspended in dry THF (12 ml) under a nitrogen atmosphere. Solid 4-[4-(3-chloro-phenylamino)-7H-pyrrolo[2,3-d]pyrimidin-6-yl]-N,N-dimethyl-benzamide (described in WO 97/02266, 140 mg, 0.37 mmol) is added and the mixture heated to 60° C. for 1 h. The reaction mixture is then hydrolized at 0° C. by sequential addition of water (0.072 ml), 15% sodium hydroxide (0.072 ml) and water (0.21 ml). The precipitate is removed by filtration and the filtrate concentrated on a rotary evaporator. The yellow crystalline residue is suspended in methanol, filtered, suspended in toluene, filtered, suspended in methanol again and filtered to give the free base of the title compound [R_f(dichloromethane/methanol 9:1 plus 1 drop of conc. ammonia)=0.36]. This is suspended in methanol (2 ml) and treated with 1 N hydrochloric acid (0.2 ml). The suspension is stirred well and filtered. The crystals are triturated in methanol/water 9:1 and filtered again to give the title compound; m.p. 280-283° C.; MS-ES⁺: (M+H)⁺=378.

Examples 80-81

The following Examples are synthesized from the corresponding amides (WO 97/02266) using an analogous procedure as described in Example 79:

| Example Number | Name | m.p. [° C.] | MS-ES+: (M + H)+ | TLC$^a$ R$_f$ | HPLC t$_R$ [min] |
|---|---|---|---|---|---|
| 80 | (3-Chloro-phenyl)-{6-[4-(4-methyl-piperazin-1-ylmethyl)-phenyl]-7H-pyrrolo[2,3-d]pyrimidin-4-yl}-amine dihydrochloride | 227-229 | 433 | 0.35 | 6.74 |
| 81 | (3-Chloro-phenyl)-[6-(4-morpholin-4-ylmethyl-phenyl)-7H-pyrrolo[2,3-d]pyrimidin-4-yl]-amine hydrochloride | 278-280 | 420 | 0.49 | 7.25 |

$^a$of the free base using dichloromethane/methanol 9:1 plus 1 drop of conc. ammonia

Example 82

2-((2-Hydroxy-ethyl)-{4-[4-((R)-1-phenyl-ethylamino)-7H-pyrrolo[2,3-d]pyrimidin-6-yl]-benzyl}-amino)-ethanol

[6-(4-Aminomethyl-phenyl)-7H-pyrrolo[2,3-d]pyrimidin-4-yl]-((R)-1-phenyl-ethyl)-amine (step 40.5, 0.5 g, 1.46 mmol) is dissolved in THF (7.5 ml) and water (0.75 ml) and cooled to −10° C. A stream of ethylene oxide is then passed through the solution for about 40 min (amount of ethylene oxide absorbed 5 to 6 g). The flask is sealed and the mixture stirred at 0° C. for 30 min and then at 50° C. for 16 h. The clear yellow solution is cooled and the solvents evaporated. The residue is purified by flash chromatography on 34 g of silica gel. The column is eluted using a mixture of dichloromethane/methanol with gradually increasing concentrations of methanol starting with 100:1.25 and ending with 100:2.5 and then switching to dichloromethane/methanol/conc. ammonia starting with 100:2.5:0.125 and ending with 100:10:0.5. Fractions containing the title compound were pooled and concentrated on a rotary evaporator. The residue is taken up in a small amount of dichloromethane and the resulting solid collected by filtration; m.p. 194-197° C.; R$_f$(dichloromethane/methanol/conc. ammonia 90:10:1)=0.21; MS-ES+: (M+H)+=432.

Example 83

3-Chloro-benzyl)-{6-[4-(4-ethyl-piperazin-1-ylmethyl)-phenyl]-7H-pyrrolo[2,3-d]pyrimidin-4-yl}-amine (3-Chloro-benzylyl)-[6-(4-chloromethyl-phenyl)-7H-pyrrolo[2,3-d]pyrimidin-4-yl]-amine (150 mg, 0.35 mmol) is suspended in 5 ml dioxane and treated with N-ethyl-piperazine. The mixture is heated to 90° C. for 7 h. The solvent is evaporated and the residue is purified by flash chromatography on 34 g of silica gel. The column is eluted using a mixture of dichloromethane/methanol with gradually increasing concentrations of methanol starting with 100:1.25 and ending with 100:5 and then switching to dichloromethane/methanol/conc. ammonia starting with 100:5:0.25 and ending with 100:10:0.5. Fractions containing the title compound were pooled and concentrated on a rotary evaporator to give the title compound; m.p. 241-243° C.; MS-ES+: (M+H)+=461.

Step 83.1: 4-[4-(3-Chloro-benzylamino)-7H-pyrrolo[2,3-d]pyrimidin-6-yl]-benzoic acid ethyl ester This compound is synthesized following an analogous procedure as described in Example 1, step 1.1 starting from 4-(4-chloro-7H-pyrrolo[2,3-d]pyrimidin-6-yl)-benzoic acid ethyl ester (WO 97/02266) and 3-chloro-benzylamine; m.p. 305-306° C.; MS-ES+: (M+H)+=407.

Step 83.2: {4-[4-(3Chloro-benzylamino)-7H-pyrrolo[2,3-d]pyrimidin-6-yl]-phenyl}methanol 2.236 g (0.059 mol) lithium aluminum hydride are suspended in 600 ml dry THF at RT. 4-[4-(3-Chloro-benzylamino)-7H-pyrrolo[2,3-d]pyrimidin-6-yl]-benzoic acid ethyl ester (4.8 g, 0.0118 mol) is added in portions over 5 min and the resulting mixture is heated to 60° C. for 1 h. The mixture is cooled in an ice bath to about 10° C. and treated sequentially with THF/water 1:1 (2.24 ml), 15% sodium hydroxide solution (4.48 ml) and water (6.72 ml). The solid aluminum complex is removed by filtration (Hyflo Super Cel®; Fluka, Buchs, Switzerland) and washed thoroughly with THF. The filtrate is concentrated to about 50 ml and the resulting suspension treated with water/ethanol 9:1 (50 ml). After stirring for 10 min the crystals were collected by filtration and dried under reduced pressure to give the title compound; m.p. 296-298° C.; MS-ES+: (M+H)+=365.

Step 83.3: (3-Chloro-benzyl)-[6-(4-chloromethyl-phenyl)-7H-pyrrolo[2,3-d]pyrimidin-4-yl]-amine A solution of 0.79 ml (10 mmol) thionylchloride in 5.5 ml of toluene is cooled to −10° C. Solid {4-[4-(3-chloro-benzylamino)-7H-pyrrolo[2,3-d]pyrimidin-6-yl]-phenyl}-methanol is added and the suspension stirred at 0° C. for 2 h and then at RT for 17 h. The solid is filtered off, washed with toluene and suspended in water (3 ml). The mixture is treated with saturated sodium bicarbonate solution (3 ml) and stirred for 10 min. The crystals are collected by filtration washed with water, a small amount of ethanol and ether and dried to give the title compound; m.p. decomposition ~300° C.; R$_f$(dichloromethane/methanol/conc. ammonia 90:10:1)=0.61; MS-ES+: (M+H)+=383.

Examples 84-107j

The following Examples are synthesized using an analogous procedure as described in Example 83:

| Example Number | Name | m.p. [° C.] | MS-ES+: (M + H)+ | TLC R$_f$ | HPLC t$_R$ [min] |
|---|---|---|---|---|---|
| 84 | (3-Chloro-benzyl)-[6-(4-dimethylaminomethyl-phenyl)-7H-pyrrolo[2,3-d]pyrimidin-4-yl]-amine | 219-222 | 393 | — | 7.46 |
| 85 | (3-Chloro-benzyl)-[6-(4-piperidin-1-ylmethyl-phenyl)-7H-pyrrolo[2,3-d]pyrimidin-4-yl]-amine | 234-235 | 432 | 0.44[a] | 795 |
| 86 | (3-Chloro-benzyl)-[6-(4-morpholin-4-ylmethyl-phenyl)-7H-pyrrolo[2,3-d]pyrimidin-4-yl]-amine | 253-254.5 | 434 | — | 7.55 |
| 87 | (3-Chloro-benzyl)-[6-(4-diethylaminomethyl-phenyl)-7H-pyrrolo[2,3-d]pyrimidin-4-yl]-amine | 231-233 | 420 | 0.35[a] | 7.86 |
| 88 | (3-Chloro-benzyl)-[6-(4-pyrrolidin-1-ylmethyl-phenyl)-7H-pyrrolo[2,3-d]pyrimidin-4-yl]-amine | 222-225 | 418 | 0.32[a] | 777 |
| 89 | (3-Chloro-benzyl)-{6-[4-(4-methyl-piperazin-1-ylmethyl)-phenyl]-7H-pyrrolo[2,3-d]pyrimidin-4-yl}-amine | 235-237 | 447 | 0.34[a] | 6.99 |
| 90 | (2-Chloro-benzyl)-[6-(4-dimethylaminomethyl-phenyl)-7H-pyrrolo[2,3-d]pyrimidin-4-yl]-amine | 256-258 | 392 | 0.30[a] | 7.65 |
| 91 | (2-Chloro-benzyl)-{6-[4-(4-ethyl-piperazin-1-ylmethyl)-phenyl]-7H-pyrrolo[2,3-d]pyrimidin-4-yl}-amine | 255-256 | 461 | 0.23[a] | 7.37 |
| 92 | (2-Chloro-benzyl)-[6-(4-piperidin-1-ylmethyl-phenyl)-7H-pyrrolo[2,3-d]pyrimidin-4-yl]-amine | 262-264 | 432 | 0.54[a] | 7.77 |
| 93 | (2-Chloro-benzyl)-[6-(4-morpholin-4-ylmethyl-phenyl)-7H-pyrrolo[2,3-d]pyrimidin-4-yl]-amine | 276-279 | 434 | 0.42 | 7.39 |
| 94 | (2-Chloro-benzyl)-{6-[4-(4-methyl-piperazin-1-ylmethyl)-phenyl]-7H-pyrrolo[2,3-d]pyrimidin-4-yl}-amine | 267-269 | 447 | 0.37[a] | 6.80 |
| 95 | (2-Chloro-benzyl)-[6-(4-pyrrolidin-1-ylmethyl-phenyl)-7H-pyrrolo[2,3-d]pyrimidin-4-yl]-amine | 264-265 | 418 | 0.33[a] | 7.59 |
| 96 | (2-Chloro-benzyl)-[6-(4-diethylaminomethyl-phenyl)-7H-pyrrolo[2,3-d]pyrimidin-4-yl]-amine | 257-258 | 420 | 0.42[a] | 7.69 |
| 97 | (2,5-Dichloro-benzyl)-{6-[4-(4-ethyl-piperazin-1-ylmethyl)-phenyl]-7H-pyrrolo[2,3-d]pyrimidin-4-yl}-amine | 249-251 | 495 | 0.30[a] | 7.44 |
| 98 | (2,5-Dichloro-benzyl)-[6-(4-dimethylaminomethyl-phenyl)-7H-pyrrolo[2,3-d]pyrimidin-4-yl]-amine | 254-257 | 426 | 0.30[a] | 7.91 |
| 99 | (2,5-Dichloro-benzyl)-[6-(4-morpholin-4-ylmethyl-phenyl)-7H-pyrrolo[2,3-d]pyrimidin-4-yl]-amine | 272-274 | 468 | 0.42[b] | 7.97 |
| 100 | (2,5-Dichloro-benzyl)-[6-(4-piperidin-1-ylmethyl-phenyl)-7H-pyrrolo[2,3-d]pyrimidin-4-yl]-amine | 258-260 | 466 | — | 8.44 |
| 101 | (2,5-Dichloro-benzyl)-[6-(4-diethylaminomethyl-phenyl)-7H-pyrrolo[2,3-d]pyrimidin-4-yl]-amine | 255-257 | 454 | 0.50[c] | 8.26 |
| 102 | (2,5-Dichloro-benzyl)-{6-[4-(4-methyl-piperazin-1-ylmethyl)-phenyl]-7H-pyrrolo[2,3-d]pyrimidin-4-yl}-amine | 244-246 | 481 | 0.37[c] | 7.43 |

-continued

| Example Number | Name | m.p. [° C.] | MS-ES+: (M + H)+ | TLC $R_f$ | HPLC $t_R$ [min] |
|---|---|---|---|---|---|
| 103 | (2,5-Dichloro-benzyl)-[6-(4-pyrrolidin-1-ylmethyl-phenyl)-7H-pyrrolo[2,3-d]pyrimidin-4-yl]-amine | 266-268 | 452 | 0.48[a] | 8.20 |
| 104 | [6-(4-Dimethylaminomethyl-phenyl)-7H-pyrrolo[2,3-d]pyrimidin-4-yl]-(3-methoxy-benzyl)-amine | 227-229 | 388 | 0.40[d] | 6.91 |
| 105 | [6-(4-Diethylaminomethyl-phenyl)-7H-pyrrolo[2,3-d]pyrimidin-4-yl]-(3-methoxy-benzyl)-amine | 230-232 | 416 | 0.57[d] | 7.36 |
| 106 | (3-Methoxy-benzyl)-[6-(4-pyrrolidin-1-ylmethyl-phenyl)-7H-pyrrolo[2,3-d]pyrimidin-4-yl]-amine | 220-222 | 414 | 0.50[d] | 7.29 |
| 107 | (3-Methoxy-benzyl)-[6-(4-piperidin-1-ylmethyl-phenyl)-7H-pyrrolo[2,3-d]pyrimidin-4-yl]-amine | 227-229 | 428 | 0.30[e] | 7.48 |
| 107a | (3-Methoxy-benzyl)-[6-(4-morpholin-4-ylmethyl-phenyl)-7H-pyrrolo[2,3-d]pyrimidin-4-yl]-amine | 263-265 | 430 | 0.42[f] | 7.02 |
| 107b | (3-Methoxy-benzyl)-{6-[4-(4-methyl-piperazin-1-ylmethyl)-phenyl]-7H-pyrrolo[2,3-d]pyrimidin-4-yl}-amine | 225-227 | 443 | 0.12[f] | 6.43 |
| 107c | {6-[4-(4-Ethyl-piperazin-1-ylmethyl)-phenyl]-7H-pyrrolo[2,3-d]pyrimidin-4-yl}-(3-methoxy-benzyl)-amine | 231-233 | 457 | 0.45[f] | 6.66 |
| 107d | (3-Methyl-benzyl)-[6-(4-piperidin-1-ylmethyl-phenyl)-7H-pyrrolo[2,3-d]pyrimidin-4-yl]-amine | 246-248 | 412 | 0.46[f] | 7.88 |
| 107e | (3-Methyl-benzyl)-[6-(4-morpholin-4-ylmethyl-phenyl)-7H-pyrrolo[2,3-d]pyrimidin-4-yl]-amine | 259-261 | 414 | 0.37[f] | 7.74 |
| 107f | [6-(4-Dimethylaminomethyl-phenyl)-7H-pyrrolo[2,3-d]pyrimidin-4-yl]-(3-methyl-benzyl)-amine | 230-232 | 372 | 0.58[d] | 7.23 |
| 107g | [6-(4-Diethylaminomethyl-phenyl)-7H-pyrrolo[2,3-d]pyrimidin-4-yl]-(3-methyl-benzyl)-amine | 241-243 | 400 | 0.6[d] | 7.71 |
| 107h | (3-Methyl-benzyl)-[6-(4-pyrrolidin-1-ylmethyl-phenyl)-7H-pyrrolo[2,3-d]pyrimidin-4-yl]-amine | 241-243 | 398 | 0.5[d] | 7.63 |
| 107i | (3-Methyl-benzyl)-{6-[4-(4-methyl-piperazin-1-ylmethyl)-phenyl]-7H-pyrrolo[2,3-d]pyrimidin-4-yl}-amine | 244-246 | 427 | 0.5[d] | 6.87 |
| 107j | {6-[4-(4-Ethyl-piperazin-1-ylmethyl)-phenyl]-7H-pyrrolo[2,3-d]pyrimidin-4-yl}-(3-methyl-benzyl)-amine | 250-252 | 441 | 0.4[d] | 6.9 |

[a] Dichloromethane/methanol/conc. ammonia 90:10:1
[b] Dichloromethane/ethanol/conc. ammonia 92:8:1
[c] Dichloromethane/ethanol/conc. ammonia 93:7:1
[d] Dichloromethane/ethanol/conc. ammonia 90:10:1
[e] Dichloromethane/methanol 80:20
[f] Dichloromethane/methanol 80:20

Example 108

Benzo[1,3]dioxol-5-yl-{6-[4-(4-methyl-piperazin-1-ylmethyl)-phenyl]-7H-pyrrolo[2,3-d]pyrimidin-4-yl}-amine A mixture of 200 mg (0.53 mmol) benzo[1,3]dioxol-5-yl-[6-(4-chloromethyl-phenyl)-7H-pyrrolo[2,3-d]pyrimidin-4-yl]-amine, 0.59 ml (5.3 mmol) 1-methyl-piperazine and a trace of NaI in 15 ml ethanol is stirred for 4 h at 65° C. and 2 h at 80° C. under $N_2$-atmosphere. The orange solution is concentrated under vacuum and the residue resolved with ethyl acetate and $NaHCO_3$-solution. The aqueous layer is separated off and extracted twice with ethyl acetate. The organic phases are washed with water and brine, dried ($MgSO_4$) and partially concentrated. Then the crystallized title compound can be filtered off; MS-ES$^+$: (M+H)$^+$=443; HPLC (conditions see Examples 67-78) $t_R$=7.1 min.

Step 108.1: [4-(4-Chloro-7H-pyrrolo[2,3-d]pyrimidin-6-yl)-phenyl]-methanol

To a suspension of 30.0 g (100 mmol) 4-(4-chtoro-7H-pyrrolo[2,3-d]pyrimidin-6-yl)-benzoic acid ethyl ester (WO 97/02266) in 450 ml dry THF at 10° C. under $N_2$-atmosphere, 500 ml -diisobutyl-aluminium hydride (1 M in THF) were added dropwise. The resulting clear solution is stirred for 1 h and then diluted with 2.1 l of dry THF. Then 98 ml of ethyl acetate are added, followed after 15 min by 45 ml of water and after 1 h by 22.5 ml of 4 N sodium hydroxide. After 1 h stirring, 200 g of $Na_2SO_4$ are added and stirring is continued for another hour. The mixture is filtered through Celite (Fluka, Buchs, Switzerland), the residue washed with THF and discarded. Concentration of the filtrate to a volume of ≈0.1 l, addition of 0.3 l of dichloromethane and filtration yields the title compound; Analysis for $C_{13}H_{10}ClN_3O$: calc. C, 60.13%; H, 3.88%; N, 16.18%; Cl, 13.65%; found C, 60.23%; H, 4.03%; N, 16.51%; Cl, 13.28%.

Step 108.2: {4-[4-(Benzo[1,3]dioxol-5ylamino)-7H-pyrrolo[2,3-d]pyrimidin-6-yl]-phenyl}-methanol A mixture of 1.5 g (5.8 mmol) of [4-(4-chloro-7H-pyrrolo[2,3-d]pyrimidin-6-yl)-phenyl]-methanol and 1.58 g (11.5 mmol) 3,4-methylendioxy-aniline in 30 ml n-butanol is stirred for 16 h at 115° C. under $N_2$ atmosphere. After cooling to ambient temperature, the title compound can be filtered off and washed with n-butanol; MS-ES$^+$: (M+H)$^+$=361; HPLC (conditions see Examples 67-78) $t_R$=8.7 min.

Step 108.3: Benzo[1,3]dioxol-5-yl-[6-(4-chloromethyl-phenyl)-7H-pyrrolo[2,3-d]pyrimidin-4-yl]-amine To a suspension of 1.83 g of {4-[4-(benzo[1,3]dioxol-5-ylamino)-7H-pyrrolo[2,3-d]pyrimidin-6-yl]-phenyl}-methanol in 56 ml of dioxane/acetonitrile 1:1 under $N_2$-atmosphere, 3.1 ml of thionylchloride are added. After 16 h stirring, the suspension is diluted with ethyl acetate and $NaHCO_3$-solution. The aqueous layer is separated off and extracted twice with ethyl acetate. The organic phases are washed with water and brine, dried ($MgSO_4$) and concentrated to yield the title compound; MS-ES$^+$: (M+H)$^+$=379; HPLC (conditions see Examples 67-78) $t_R$ =11.4 min.

Examples 108a-114

The following Examples are synthesized using an analogous procedure as described in Example 108:

| Example Number | Name | m.p. [° C.] | MS-ES$^+$: (M + H)$^+$ | TLC $R_f$ | HPLC$^a$ $t_R$ [min] |
|---|---|---|---|---|---|
| 108a | Benzo[1,3]dioxol-5-yl-{6-[4-(4-ethyl-piperazin-1-ylmethyl)-phenyl]-7H-pyrrolo[2,3-d]pyrimidin-4-yl}-amine | | 457 | 0.32$^c$ | 7.3 |
| 109 | Benzo[1,3]dioxol-5-yl-[6-(4-dimethylaminomethyl-phenyl)-7H-pyrrolo[2,3-d]pyrimidin-4-yl]-amine | | 388 | 0.08$^b$ | 7.6 |
| 110 | Benzo[1,3]dioxol-5-yl-[6-(4-morpholin-4-ylmethyl-phenyl)-7H-pyrrolo[2,3-d]pyrimidin-4-yl]-amine | | 430 | 0.16$^b$ | 7.7 |
| 111 | (6-Methoxy-pyridin-3-yl)-[6-(4-morpholin-4-ylmethyl-phenyl)-7H-pyrrolo[2,3-d]pyrimidin-4-yl]-amine | 263-264 | 417 | 0.78$^c$ | 7.2 |
| 112 | (6-Methoxy-pyridin-3-yl)-{6-[4-(4-methyl-piperazin-1-ylmethyl)-phenyl]-7H-pyrrolo[2,3-d]pyrimidin-4-yl}-amine | 241-242 | 430 | 0.07$^b$ | 6.9 |
| 113 | (6-Methoxy-pyridin-3-yl)-{6-[4-(dimethylamino-methyl)-phenyl]-7H-pyrrolo[2,3-d]pyrimidin-4-yl}-amine | | 375 | 0.49$^c$ | 7.0 |

-continued

| Example Number | Name | m.p. [° C.] | MS-ES⁺: (M + H)⁺ | TLC R_f | HPLC[a] t_R [min] |
|---|---|---|---|---|---|
| 114 | (6-Methoxy-pyridin-3-yl)-{6-[4-(4-ethyl-piperazin-1-ylmethyl)-phenyl]-7H-pyrrolo[2,3-d]pyrimidin-4-yl}-amine | | 444 | 0.41[c] | 6.8 |

[a]HPLC: conditions see Examples 67-78
[b]Dichloromethane/methanol/conc. ammonia 90:10:1
[c]THF/methanol/conc. ammonia 90:10:1

Example 115

5-[6-(4-Morpholin-4-ylmethyl-phenyl)-7H-pyrrolo[2,3-d]pyrimidin-4-ylamino]-1H-pyridin-2-one To 84 mg (0.20 mmol) of (6-methoxy-pyridin-3-yl)-[6-(4-morpholin-4-ylmethyl-phenyl)-7H-pyrrolo[2,3-d]pyrimidin-4-yl]-amine and 10 ml chloroform in an ampoule under $N_2$-atmosphere, 0.1 ml (0.73 mmol) $Me_3Sil$ is added. After stirring for 6 h at 70° C., diluted $NaHCO_3$ solution and EtOAc is added to the suspension at RT. Stirring, filtration and washing with water yields the title compound; TLC (THF/methanol/conc. ammonia 90:10:1) $R_f$=0.23; MS-ES⁺: (M+H)⁺=403; HPLC (conditions see Examples 67-78) $t_R$=4.7 min.

Examples 116-118

The following Examples are synthesized using an analogous procedure as described in Example 115 (eventually after purification with chromatography on $SiO_2$ or reversed phase medium pressure liquid chromatography: Nucleosil $C_{18}$, $CH_3CN/H_2O$+TFA):

| Example Number | Name | MS-ES⁺: (M + H)⁺ | TLC R_f | HPLC[a] t_R [min] |
|---|---|---|---|---|
| 116 | 5-[6-(4-Dimethylaminomethyl-phenyl)-7H-pyrrolo[2,3-d]pyrimidin-4-ylamino]-1H-pyridin-2-one | 361 | 0.09[d] | 9.2[b] |
| 117 | 5-{6-[4-(4-Methyl-piperazin-1-ylmethyl)-phenyl]-7H-pyrrolo[2,3-d]pyrimidin-4-ylamino}-1H-pyridin-2-one | 416 | | 9.0[c] |
| 118 | 5-{6-[4-(4-Ethyl-piperazin-1-ylmethyl)-phenyl]-7H-pyrrolo[2,3-d]pyrimidin-4-ylamino}-1H-pyridin-2-one | 430 | | 9.1[c] |

[a]HPLC: solvent system: a): Acetonitrile + 0.05% TFA; b): water + 0.05% TFA.
[b]Grad: 20% → 100% a) in b) for 13 min + 5 min 100% a).
[c]Grad: 5% → 40% a) in b) for 9 min + 7 min 40% a).
[d]THF/methanol/conc. ammonia 90:10:1

Example 119

(6-Methoxy-pyridin-3-ylmethyl)-{6-[4-(4-ethyl-piperazin-1-ylmethyl)-phenyl]-7H-pyrrolo[2,3-d]pyrimidin-4-yl}-amine (6-Methoxy-pyridin-3-ylmethyl)-[6-(4-chloromethyl-phenyl)-7H-pyrrolo[2,3-d]pyrimidin-4-yl]-amine (400 mg, 1.05 mMol), 1.34 ml N-ethyl-piperazine and a trace of NaI is stirred for 2.5 h in 30 ml boiling ethanol. The solvent is evaporated and the residue is re-dissolved in EtOAc and diluted $NaHCO_3$-solution. The separated aqueous layer is re-extracted with EtOAc and the organic phases are washed with water and brine, dried ($Na_2SO_4$) and partially concentrated in vacuuo. The title compound crystallizes and can be filtered off; MS-ES⁺: (M+H)⁺=458; elemental analysis for C, H, and N, within 0.5% of calculated value.

Step 119.1: 4-[4-(6-Methoxy-pyridin-3-ylmethylamino)-7H-pyrrolo[2,3-d]pyrimidin-6-yl]-benzoic acid ethyl ester A mixture of 5.0 g (16.6 mMol) 4-(4-chloro-7H-pyrrolo[2,3-d]pyrimidin-6-yl)benzoic acid ethyl ester (WO 97/02266) and 2.52 g (18 mMol) of 6-methoxy-pyridin-3-ylmethylamine (CAS: 262295-96-5; prepared from 6-methoxy-nicotin-nitrile by hydrogenation in the presence of Raney-Nickel in methanol containing $NH_3$) in 3.5 ml (25 mMol) of $Et_3N$ and 100 ml n-butanol is heated for 8 h to 140° C. Then additional 0.69 g of 6-methoxy-pyridin-3-ylmethylamine and 1.2 ml of $Et_3N$ are added. Heating is continued for 6 h and the hot suspension filtrated and the residue washed with n-butanol and hexane to give the title compound; m.p. 305° C.; elemental analysis for C, H, and N, within 0.5% of calculated value.

Step 119.2: {4-[4-(6-Methoxy-pyridin-3-ylmethylamino)-7H-pyrrolo[2,3-d]pyrimidin-6-yl]-phenyl}-methanol 5.0 g (12 mMol) of 4-[4-(6-methoxy-pyridin-3-ylmethylamino)-7H-pyrrolo[2,3-d]pyrimidin-6-yl]-benzoic acid ethyl ester in 200 ml of THF is cooled to −10° C. Then 80 ml of a 1 N solution of di-isobutyl-aluminium hydride in THF are added dropwise. After stirring for 3 h at RT, 200 ml of THF and 100 ml of EtOAc are added, followed by 10 ml of a 10%-solution of $NH_4Cl$ in water. After 30 min vigorous stirring, 20 g of $Na_2SO_4$ are added, then the mixture is filtered through Celite. Concentration of the filtrate, stirring in methanol and filtration gives the title compound; MS-ES⁺: (M+H)⁺=362.

Step 119.3: (6-Methoxy-pyridin-3-ylmethyl)-[6-(4-chloromethyl-phenyl)-7H-pyrrolo[2,3-d]pyrimidin-4-yl]-amine A suspension of 3.28 g (9.1 mMol) of {4-[4-(6-methoxy-pyridin-3-ylmethylamino)-7H-pyrrolo[2,3-d]pyrimidin-6-yl]-phenyl}-methanol in 40 ml of acetonitrile, 40 ml of dioxane and 4 ml of $SOCl_2$ is stirred for 1 h at RT. The mixture is dissolved in EtOAc and $NaHCO_3$-solution, the aqueous layer separated off and extracted with EtOAc. The organic layers are washed with $NaHCO_3$-solution, water and brine, dried ($Na_2SO_4$) and partially concentrated. The crystallized title compound can be filtered off, elemental analysis for C, H, and N, within 0.4%; of calculated value.

Examples 120-125

The following Examples are synthesized analogously:

| Example Number | Name | m.p. [° C.] | MS-ES⁺: (M + H)⁺ | HPLC[a] $t_R$ [min] | Elem. anal.[b] |
|---|---|---|---|---|---|
| 120 | (6-Methoxy-pyridin-3-ylmethyl)-{6-[4-(morpholin-4-ylmethyl)-phenyl]-7H-pyrrolo[2,3-d]pyrimidin-4-yl}-amine | | 431 | 7.2 | CHN |
| 121 | (6-Methoxy-pyridin-3-ylmethyl)-{6-[4-(dimethylamino-methyl)-phenyl]-7H-pyrrolo[2,3-d]pyrimidin-4-yl}-amine | | 389 | 7.1 | CHN |
| 122 | (2-Methoxy-pyridin-4-ylmethyl)-{6-[4-(4-ethyl-piperazin-1-ylmethyl)-phenyl]-7H-pyrrolo[2,3-d]pyrimidin-4-yl}-amine[c] | 210-212 | 458 | 6.6 | |
| 123 | (2-Methoxy-pyridin-4-ylmethyl)-{6-[4-(morpholin-4-ylmethyl)-phenyl]-7H-pyrrolo[2,3-d]pyrimidin-4-yl}-amine[c] | | 431 | 7.0 | |
| 124 | (2-Methoxy-pyridin-4-ylmethyl)-{6-[4-(dimethylamino-methyl)-phenyl]-7H-pyrrolo[2,3-d]pyrimidin-4-yl}-amine[c] | 210-211 | 389 | 6.8 | CHN |
| 125 | (2-Methoxy-pyridin-4-ylmethyl)-{6-[4-(4-methyl-piperazin-1-ylmethyl)-phenyl]-7H-pyrrolo[2,3-d]pyrimidin-4-yl}-amine[c] | 211-212 | 444 | 6.3 | CHN |

[a]HPLC: solvent system: a): Acetonitrile + 0.05% TFA; b): water + 0.05% TFA: Grad: 20% → 100% a) in b) for 13 min + 5 min 100% a).
[b]experimental value within 0.4% of calculated one
[c]2-Methoxy-pyridin-4-ylmethylamine used [preparation see J. Med. Chem. 36 (1993), 2362]

Examples 126-132

Cleavage of the methylether of the above compounds analogously to Example 115 gives:

| Example Number | Name | m.p. [° C.] | MS-ES⁺: (M + H)⁺ | HPLC[a] $t_R$ [min] | Elem. anal.[d] |
|---|---|---|---|---|---|
| 126 | 5-({6-[4-(4-Ethyl-piperazin-1-ylmethyl)-phenyl]-7H-pyrrolo[2,3-d]pyrimidin-4-ylamino}-methyl)-1H-pyridin-2-one | | 444 | 9.4[b] | |
| 127 | 5-({6-[(4-(Dimethylamino-methyl)-phenyl]-7H-pyrrolo[2,3-d]pyrimidin-4-ylamino}-methyl)-1H-pyridin-2-one | | 375 | 9.6[b] | CHN |
| 128 | 5-({6-[4-(4-Morpholin-ylmethyl)-phenyl]-7H-pyrrolo[2,3-d]pyrimidin-4-ylamino}-methyl)-1H-pyridin-2-one | | 417 | 9.7[b] | CHN |
| 129 | 4-({6-[4-(4-Ethyl-piperazin-1-ylmethyl)-phenyl]-7H-pyrrolo[2,3-d]pyrimidin-4-ylamino}-methyl)-1H-pyridin-2-one | 291-292 | 444 | 9.4[b] | |
| 130 | 4-({6-[4-(4-Morpholin-ylmethyl)-phenyl]-7H-pyrrolo[2,3-d]pyrimidin-4-ylamino}-methyl)-1H-pyridin-2-one | | 417 | 5.7[c] | CHN |
| 131 | 4-({6-[(4-(Dimethylamino-methyl)-phenyl]-7H-pyrrolo[2,3-d]pyrimidin-4-ylamino}-methyl)-1H-pyridin-2-one | 330-332 | 375 | 5.6[c] | CHN |

-continued

| Example Number | Name | m.p. [° C.] | MS-ES+: (M + H)+ | HPLC[a] t_R [min] | Elem. anal.[d] |
|---|---|---|---|---|---|
| 132 | 4-({6-[4-(4-Methyl-piperazin-1-ylmethyl)-phenyl]-7H-pyrrolo[2,3-d]pyrimidin-4-ylamino}-methyl)-1H-pyridin-2-one | | | 5.0[c] | CHN |

[a]HPLC: solvent system: a): Acetonitrile + 0.05% TFA; b): water + 0.05% TFA.
[b]Grad: 5% → 40% a) in b) for 9 min + 7 min 40% a).
[c]Grad: 20% → 100% a) in b) for 13 min + 5 min 100% a).
[d]experimental value within 0.4% of calculated one Example 133

(2-Methoxy-pyridin-4-yl)-[6-(4-morpholin-4-ylmethyl-phenyl)-7H-pyrrolo[2,3-d]pyrimidin-4-yl]-amine 330 mg (0.90 mMol) (2-Methoxy-pyridin-4-yl)-[6-(4-chloromethyl-phenyl)-7H-pyrrolo[2,3-d]pyrimidin-4-yl]-amine, 0.81 ml morpholine and a trace of NaI is stirred for 2 h in 20 ml boiling ethanol. A clear solution is formed from which upon cooling to RT the title compound crystallizes out and can be filtered off; TLC (CH$_2$Cl$_2$/methanol 9:1) R$_f$=0.33; MS-ES+: (M+H)+=417.

Step 133.1: {4-[4-(2-Methoxy-pyridin-4-ylamino)-7H-pyrrolo[2,3-d]pyrimidin-6-yl]-phenyl}-methanol To 4.16 g (16 mMol) of [4-(4-chloro-7H-pyrrolo[2,3-d]pyrimidin-6-yl)-phenyl]-methanol (see Step 108.3) and 1.99 g (16 mMol) of 2-methoxy-pyridin-4-ylamine [see *Rec. Trav. Chim.* (1955) 74, 1160; prepared from 2-methoxy-4-nitro-pyridine-1-oxide by hydrogenation in the presence of Raney-Nickel in methanol/THF] in 90 ml degassed DMF under N$_2$-atmosphere, 996 mg of R(+)-BINAP [R(+)-2,2'-bis-(diphenylphosphino)-1,1'-binaphthalin]; 1.6 mMol], 414 mg Pd$_2$(dba)$_3$·CHCl$_3$ [tris(dibenzylideneacetone)dipalladium (0) chloroform complex; 0.40 mMol] and 3.08 g (32 mMol) of sodium-tert-butylate are subsequently added. The red solution is stirred at 70° C. over night and then poured into a mixture of 0.5 l of EtOAc and 1 l buffer (7.8 g of NaH$_2$PO$_4$·2H$_2$O, 5 g of Na$_2$HPO$_4$·2H$_2$O in 1 l H$_2$O). After stirring for 1 h, the title compound is filtered off and washed with water and EtOAc; HPLC (conditions see Examples 67-78) t$_R$=8.2 min; MS-ES+: (M+H)+=348.

Step 133.2: (2-Methoxy-pyridin-4-yl)-[6-(4-chloromethyl-phenyl)-7H-pyrrolo[2,3-d]pyrimidin-4-yl]-amine At 0° C., a suspension of 1.23 g (3.5 mMol) of {4-[4-(2-methoxy-pyridin-4-ylamino)-7H-pyrrolo[2,3-d]pyrimidin-6-yl]-phenyl}-methanol in 18 ml of acetonitrile, 18 ml of dioxane and 1.5 ml of SOCl$_2$ is prepared at 0° C. and then stirred for 4.5 h at RT. The mixture is diluted with 0.2 l of EtOAc and 0.1 l of saturated NaHCO$_3$-solution, stirred and the title compound off; MS-ES+: (M+H)+=366. More product can be obtained by extraction of the filtrate.

Examples 134-140

The following Examples are synthesized by preparing the corresponding methoxy pyridines analogously to Example 133 followed by de-methylation to the corresponding pynidones as described in Example 115:

| Example Number | Name | MS-ES+ (M + H)+ | HPLC[a] t_R [min] | Elem. anal.[b] | TLC R_f |
|---|---|---|---|---|---|
| 134 | 4-[6-(4-Morpholin-4-ylmethyl-phenyl)-7H-pyrrolo[2,3-d]pyrimidin-4-ylamino]-1H-pyridin-2-one | 403 | 7.3 | | 0.24[c] |
| 135 | (2-Methoxy-pyridin-4-yl)-{6-[4-(4-methyl-piperazin-1-ylmethyl)-phenyl]-7H-pyrrolo[2,3-d]pyrimidin-4-yl}-amine | 430 | 7.2 | | 0.35[c] |
| 136 | 4-{6-[4-(4-Methyl-piperazin-1-ylmethyl)-phenyl]-7H-pyrrolo[2,3-d]pyrimidin-4-ylamino}-1H-pyridin-2-one | 416 | 7.0 | | 0.08[c] |
| 137 | (2-Methoxy-pyridin-4-yl)-{6-[4-(4-ethyl-piperazin-1-ylmethyl)-phenyl]-7H-pyrrolo[2,3-d]pyrimidin-4-yl}-amine | 444 | 7.7 | | 0.48[d] |
| 138 | 4-{6-[4-(4-Ethyl-piperazin-1-ylmethyl)-phenyl]-7H-pyrrolo[2,3-d]pyrimidin-4-ylamino}-1H-pyridin-2-one | 430 | 7.2 | | 0.10[c] |
| 139 | [6-(4-Dimethylaminomethyl-phenyl)-7H-pyrrolo[2,3-d]pyrimidin-4-yl]-(2-methoxy-pyridin-4-yl)-amine | 375 | 7.2 | CHN | 0.47[d] |

-continued

| Example Number | Name | MS-ES+: (M + H)+ | HPLCa tR [min] | Elem. anal.b | TLC Rf |
|---|---|---|---|---|---|
| 140 | 4-[6-(4-Dimethylaminomethyl-phenyl)-7H-pyrrolo[2,3-d]pyrimidin-4-ylamino]-1H-pyridin-2-one | 361 | 7.2 | | 0.08c | aHPLC: solvent system: a): Acetonitrile + 0.05% TFA; b): water + 0.05% TFA. Grad: 20% → 100% a) in b) for 13 min + 5 min 100% a).
bexperimental value within 0.4% of calculated one
c$CH_2Cl_2$/MeOH/$NH_3^{conc.}$ 80:20:1
dTHF/MeOH/$NH_3^{conc.}$ 90:10:0.3

Example 141

6-[4-(4-Ethyl-piperazin-1-ylmethyl)-phenyl]-4-(4-fluoro-2-methyl-1H-indol-5-yloxy)-7H-pyrrolo[2,3-d]pyrimidine 1.56 ml of diisobutyl-aluminium hydride (1 M in THF) are added to a solution of 130 mg (0.26 mMol) of (4-ethyl-piperazin-1-yl)-{4-[4-(4-fluoro-2-methyl-1H-indol-5-yloxy)-7H-pyrrolo[2,3-d]pyrimidin-6-yl]-phenyl}methanone in 13 ml of THF at −15° C. under a $N_2$-atmosphere. After 3 h, 4 ml of EtOAc are added to the solution, followed by 0.2 ml of a saturated solution of $NH_4Cl$ in water. After adding solid $Na_2SO_4$, the reaction mixture is filtered through Celite. The filtrate is concentrated together with 3 g of $SiO_2$. The resulting powder is put on top of a chromatography column ($SiO_2$) and then eluted with EtOAc/methanol 4:1 and finally EtOAc/methanol/$NEt_3$ 80:20:1, yielding the title compound; HPLC (conditions see Examples 67-78) $t_R$=10.5 min; MS-ES+: (M+H)+=485.

Step 141.1: 4-[4-Chloro-1-(4-methox-benzyl)-1H-pyrrolo[2,3-d]pyrimidin-6-yl]-benzoic acid ethyl ester A suspension of 3.0 g (10 mMol) of 4-(4-chloro-7H-pyrrolo[2,3-d]pyrimidin-6-yl)-benzoic acid ethyl ester (WO 97/02266), 2.4 g (17 mMol) of $K_2CO_3$, 0.32 g (1 mMol) of tetrabutyl-ammoniumbromide and 2.0 ml (15 mMol) of 4-methoxy-benzylchloride in 25 ml of 2-butanone is stirred for 18 h at 80° C. Then the suspension is filtered, the residue washed with 2-butanone and discarded. The filtrate is diluted with EtOAc and water, the aqueous layer separated off and extracted twice with EtOAc. The organic layers are washed with water and brine, dried ($Na_2SO_4$) and concentrated after adding 13 g of $SiO_2$. The resulting powder is put on top of a chromatography column ($SiO_2$) and then eluted with hexane/EtOAc 2:1. 4-[4-Chloro-7-(4-methoxy-benzyl)-7H-pyrrolo[2,3-d]pyrimidin-6-yl]-benzoic acid ethyl ester [TLC (hexane/EtOAc 2:1) $R_f$=0.40; MS-ES+: (M+H)+=422] is eluated first, followed by the title compound; TLC (hexane/EtOAc 2:1) $R_f$=0.23; MS-ES+: (M+H)+=422.

Step 141.2: 4-[4-(4-Fluoro-2-methyl-1H-indol-5-yloxy)-1-(4-methoxy-benzyl)-1H-pyrrolo[2,3-d]pyrimidin-6-yl]-benzoic acid ethyl ester A mixture of 3.96 g (9.4 mMol) of 4-[4-chloro-1-(4-methoxy-benzyl)-1H-pyrrolo[2,3-d]pyrimidin-6-yl]-benzoic acid ethyl ester, 2.14 g (13 mMol) of 4-fluoro-5-hydroxy-2-methyl-1H-indole (preparation see WO 00/47212; Ex. 237) and 2.44 (17.7 mMol) of $K_2CO_3$ in 90 ml of DMF is heated for 9 h at 95° C. The reaction mixture is concentrated in vacuuo, the residue dissolved in EtOAc and water, the aqueous layer separated off and extracted twice with EtOAc. The organic layers are washed with water and brine, dried ($Na_2SO_4$) and concentrated. Column chromatography ($SiO_2$, EtOAc/hexane 1:1) gives the title compound; TLC (EtOAc/hexane 1:1) $R_f$=0.24; MS-ES+: (M+H)+=551.

Step 141.3: 4-[4-(4-Fluoro-2-methyl-1H-indol-5-yloxy)-7H-pyrrolo[2,3-d]pyrimidin-6-yl]-benzoic acid ethyl ester Hydrogenation of 0.50 g (0.91 mMol) of 4-[4-(4-fluoro-2-methyl-1H-indol-5-yloxy)-1-(4-methoxy-benzyl)-1H-pyrrolo[2,3-d]pyrimidin-6-yl]-benzoic acid ethyl ester in 150 ml of THF and 15 ml of 1,3-dimethyl-2-imidazolidinone in the presence of 0.2 g of Pd/C (10%; "Engelhard 5125"), filtration and concentration gives the crude product. Stirrng in THF/water, filtration and washing with water gives the title compound; MS-ES+: (M+H)+=431; elemental analysis for C, H, N, and ,F within 0.4%; of calculated value.

Step 141.4: 4-[4-(4-Fluoro-2-methyl-1H-indol-5-yloxy)-7H-pyrrolo[2,3-d]pyrimidin-6-yl]-benzoic acid lithium salt A suspension of 2.87 g (6.7 mMol) of 4-[4-(4-fluoro-2-methyl-1H-indol-5-yloxy)-7H-pyrrolo[2,3-d]pyrimidin-6-yl]-benzoic acid ethyl ester and 520 mg (12 mMol) $LiOH.H_2O$ in 240 ml of dioxane and 5 ml of water is stirred for 24 h at 120° C. The solid is dissolved first, then a new precipitate is formed. Filtration at RT and washing with dioxane and diethylether gives the title compound; HPLC (conditions see Examples 67-78) $t_R$=13.5 min; MS-ES+: (M+H)+=403.

Step 141.5: (4-Ethyl-piperazin-1-yl)-{4-[4-(4-fluoro-2-methyl-1H-indol-5-yloxy)-7H-pyrrolo[2,3-d]pyrimidin-6-yl]-phenyl}-methanone To 340 mg (0.83 mMol) 4-[4-(4-fluoro-2-methyl-1H-indol-5-yloxy)-7H-pyrrolo[2,3-d]pyrimidin-6-yl]-benzoic acid lithium salt in 5 ml of DMF under $N_2$-atmosphere, 0.38 ml (3 mMol) of N-ethylpiperazine and 0.31 ml (95%; 2 mMol) of diethyl-cyanphosphonate are added at 0° C. After 60 min, the suspension is diluted with EtOAc and washed with saturated $NaHCO_3$-solution, water and brine. The aqueous layers are reextracted twice with EtOAc, the organic layers dried ($Na_2SO_4$) and concentrated after adding $SiO_2$. The resulting powder is put on top of a chromatography column ($SiO_2$) and the title compound eluted with EtOAc/methanol/$NH_3^{conc.}$ 80:20:1; HPLC (conditions see Examples 67-78) $t_R$=10.4 min; MS-ES+: (M+H)+=499.

Examples 142-144

The following Examples are synthesized analogously to Example 141:

| Example Number | Name | MS-ES+: (M + H)+ | HPLC[a] t_R [min] | Elem. anal.[b] | m.p. [° C.] | TLC R_f |
|---|---|---|---|---|---|---|
| 142 | 6-[4-(4-Methyl-piperazin-1-ylmethyl)-phenyl]-4-(4-fluoro-2-methyl-1H-indol-5-yloxy)-7H-pyrrolo[2,3-d]pyrimidine | 471 | 12.8 | CHNF | | |
| 143 | 4-(4-Fluoro-2-methyl-1H-indol-5-yloxy)-6-(4-morpholin-4-ylmethyl-phenyl)-7H-pyrrolo[2,3-d]pyrimidine | 458 | 10.7 | | 280-282 | 0.19[c] |
| 144 | {4-[4-(4-Fluoro-2-methyl-1H-indol-5-yloxy)-7H-pyrrolo[2,3-d]pyrimidin-6-yl]-benzyl}-dimethyl-amine | 416 | 10.7 | | | 0.21[d] |

[a]HPLC: solvent system: a): Acetonitrile + 0.05% TFA; b): water + 0.05% TFA. Grad: 20% → 100% a) in b) for 13 min + 5 min 100% a).
[b]experimental value within 0.4% of calculated one
[c]EtOAc/MeOH 19:1
[d]EtOAc/MeOH/NEt_3 80:20:1

Example 145

Dry-filled Capsules 5000 capsules, each comprising as active ingredient 0.25 g of one of the compounds of formula I mentioned in the preceding Examples, are prepared as follows:

| Composition | |
|---|---|
| active ingredient | 1250 g |
| talcum | 180 g |
| wheat starch | 120 g |
| magnesium stearate | 80 g |
| lactose | 20 g |

Preparation process: The mentioned substances are pulverised and forced through a sieve of 0.6 mm mesh size. 0.33 g portions of the mixture are introduced into gelatin capsules using a capsule-filling machine.

Example 146

Soft Capsules 5000 soft gelatin capsules, each comprising as active ingredient 0.05 g of one of the compounds of formula I mentioned in the preceding Examples, are prepared as follows:

| Composition | |
|---|---|
| active ingredient | 250 g |
| PEG 400 | 1 liter |
| Tween 80 | 1 liter |

Preparation process: The active ingredient is pulverised and suspended in PEG 400 (polyethylene glycol having an M_r. of from approx. 380 to approx. 420, Fluka, Switzerland) and Tween®80 (polyoxyethylene sorbitan monolaurate, Atlas Chem. Ind. Inc., USA, supplied by Fluka, Switzerland) and ground in a wet pulveriser to a particle size of approx. from 1 to 3 μm. 0.43 g portions of the mixture are then introduced into soft gelatin capsules using a capsule-filling machine.

Example 147

Inhibition of the Tyrosine Kinase Activity of EGF-R (HER-1), ErbB-2 (HER-2) and VEGF Receptor (KDR)

The inhibition tests are carried out as described above. The $IC_{50}$ values for some of the compounds of formula I are given below:

| Compound from Example No. | HER-1 $IC_{50}$ [μM] | HER-2 $IC_{50}$ [μM] | KDR $IC_{50}$ [μM] |
|---|---|---|---|
| 3 | 0.0031 | 0.008 | 0.0107 |
| 4 | 0.0031 | 0.0072 | 0.0093 |
| 5 | 0.0031 | 0.0067 | 0.006 |
| 6 | 0.007 | 0.005 | 0.0127 |
| 7 | 0.004 | 0.011 | 0.058 |
| 8a | 0.0024 | 0.0094 | 0.017 |
| 10 | 0.004 | 0.009 | 0.0293 |
| 11 | 0.0043 | 0.005 | 0.0497 |
| 12 | 0.0047 | 0.005 | 0.1387 |
| 13 | 0.006 | 0.005 | 0.088 |
| 14 | 0.0063 | 0.0085 | 0.0927 |
| 15 | 0.005 | 0.0065 | 0.0493 |
| 16a | 0.0012 | 0.016 | 0.061 |
| 18 | 0.0165 | 0.0315 | 0.0245 |
| 43 | 0.005 | 0.0115 | 0.0515 |
| 48 | 0.0057 | 0.0075 | 0.058 |
| 52 | 0.0157 | 0.014 | 0.125 |
| 86 | 0.0055 | 0.016 | 0.105 |
| 94 | 0.0018 | 0.016 | 0.042 |
| 107f | 0.0025 | 0.045 | 0.019 |
| 116 | 0.039 | 0.0155 | 0.0155 |

What is claimed is:

1. A compound selected from the group consisting of
(3-chloro-4-fluoro-phenyl)-(6-{4-[(tetrahydro-pyran-4-ylamino)-methyl]-phenyl}-7H-pyrrolo[2,3-d]pyrimidin-4-yl)-amine;
(3-chloro-4-fluoro-phenyl)-(6-{4-[(2-morpholin-4-yl-ethylamino)-methyl]-phenyl}-7H-pyrrolo[2,3-d]pyrimidin-4-yl)-amine;

N-{4-[4-(3-chloro-4-fluoro-phenylamino)-7H-pyrrolo[2,3-d]pyrimidin-6-yl]-benzyl}-N',N'-diethyl-ethane-1,2-diamine;
(3-chloro-4-fluoro-phenyl)-{6-[4-(isopropylamino-methyl)-phenyl]-7H-pyrrolo[2,3-d]pyrimidin-4-yl}-amine;
(6-{4-[(2-morpholin-4-yl-ethylamino)-methyl]-phenyl}-7H-pyrrolo[2,3-d]pyrimidin-4-yl)-((R)-1-phenyl-ethyl)-amine;
((R)-1-phenyl-ethyl)-(6-{4-[(tetrahydro-pyran-4-ylamino)-methyl]-phenyl}-7H-pyrrolo[2,3-d]pyrimidin-4-yl)-amine;
N,N-diethyl-N'-{4-[4-((R)-1-phenyl-ethylamino)-7H-pyrrolo[2,3-d]pyrimidin-6-yl]-benzyl}-ethane-1,2-diamine;
{6-[4-(tert-butylamino-methyl)-phenyl]-7H-pyrrolo[2,3-d]pyrimidin-4-yl}-((R)-1-phenyl-ethyl)-amine;
{6-[4-(isopropylamino-methyl)-phenyl]-7H-pyrrolo[2,3-d]pyrimidin-4-yl}-((R)-1-phenyl-ethyl)-amine;
[6-(4-ethylaminomethyl-phenyl)-7H-pyrrolo[2,3-d]pyrimidin-4-yl]-((R)-1-phenyl-ethyl)-amine;
[6-(4-methylaminomethyl-phenyl)-7H-pyrrolo[2,3-d]pyrimidin-4-yl]-((R)-1-phenyl-ethyl)-amine;
(3-methoxy-benzyl)-[6-(4-morpholin-4-ylmethyl-phenyl)-7H-pyrrolo[2,3-d]pyrimidin-4-yl]-amine;
(3-methoxy-benzyl)-{6-[4-(4-methyl-piperazin-1-ylmethyl)-phenyl]-7H-pyrrolo[2,3-d]pyrimidin-4-yl}-amine;
{6-[4-(4-ethyl-piperazin-1-ylmethyl)-phenyl]-7H-pyrrolo[2,3-d]pyrimidin-4-yl}-(3-methoxy-benzyl)-amine;
(3-methyl-benzyl)-[6-(4-piperidin-1-ylmethyl-phenyl)-7H-pyrrolo[2,3-d]pyrimidin-4-yl]-amine;
(3-methyl-benzyl)-[6-(4-morpholin-4-ylmethyl-phenyl)-7H-pyrrolo[2,3-d]pyrimidin-4-yl]-amine;
[6-(4-dimethylaminomethyl-phenyl)-7H-pyrrolo[2,3-d]pyrimidin-4-yl]-(3-methyl-benzyl)-amine;
[6-(4-diethylaminomethyl-phenyl)-7H-pyrrolo[2,3-d]pyrimidin-4-yl]-(3-methyl-benzyl)-amine;
(3-methyl-benzyl)-[6-(4-pyrrolidin-1-ylmethyl-phenyl)-7H-pyrrolo[2,3-d]pyrimidin-4-yl]-amine;
(3-methyl-benzyl)-{6-[4-(4-methyl-piperazin-1-ylmethyl)-phenyl]-7H-pyrrolo[2,3-d]pyrimidin-4-yl}-amine;
{-6-[4-(4-ethyl-piperazin-1-ylmethyl)-phenyl]-7H-pyrrolo[2,3-d]pyrimidin-4-yl}-(3-methyl-benzyl)-amine;
benzo[1,3]dioxol-5-yl-{6-[4-(4-ethyl-piperazin-1-ylmethyl)-phenyl]-7H-pyrrolo[2,3-d]pyrimidin-4-yl}-amine;
(6-methoxy-pyridin-3-yl)-{6-[4-(4-ethyl-piperazin-1-ylmethyl)-phenyl]-7H-pyrrolo[2,3-d]pyrimidin-4-yl}-amine;
5-{6-[4-(4-ethyl-piperazin-1-ylmethyl)-phenyl]-7H-pyrrolo[2,3-d]pyrimidin-4-ylamino}-1H-pyridin-2-one;
(6-methoxy-pyridin-3-ylmethyl)-{6-[4-(4-ethyl-piperazin-1-ylmethyl)-phenyl]-7H-pyrrolo[2,3-d]pyrimidin-4-yl}-amine;
(6-methoxy-pyridin-3-ylmethyl)-{6-[4-(morpholin-4-ylmethyl)-phenyl]-7H-pyrrolo[2,3-d]pyrimidin-4-yl}-amine;
(6-methoxy-pyridin-3-ylmethyl)-{6-[4-(dimethylamino-methyl)-phenyl]-7H-pyrrolo[2,3-d]pyrimidin-4-yl}-amine;
(2-methoxy-pyridin-4-ylmethyl)-{6-[4-(4-ethyl-piperazin-1-ylmethyl)-phenyl]-7H-pyrrolo[2,3-d]pyrimidin-4-yl}-amine;
(2-methoxy-pyridin-4-ylmethyl)-{6-[4-(morpholin-4-ylmethyl)-phenyl]-7H-pyrrolo[2,3-d]pyrimidin-4-yl}-amine;
(2-methoxy-pyridin-4-ylmethyl)-{6-[4-(dimethylamino-methyl)-phenyl]-7H-pyrrolo[2,3-d]pyrimidin-4-yl}-amine;
(2-methoxy-pyridin-4-ylmethyl)-{6-[4-(4-ethyl-piperazin-1-ylmethyl)-phenyl]-7H-pyrrolo[2,3-d]pyrimidin-4-yl}-amine;
5-({6-[4-(dimethylamino-methyl)-phenyl]-7H-pyrrolo[2,3-d]pyrimidin-4-ylamino}-methyl)-1H-pyridin-2-one;
5-({6-[4-(4-morpholin-ylmethyl)-phenyl]-7H-pyrrolo[2,3-d]pyrimidin-4-ylamino}-methyl)-1H-pyridin-2-one;
4-({6-[4-(4-ethyl-piperazin-1-ylmethyl)-phenyl]-7H-pyrrolo[2,3-d]pyrimidin-4-ylamino}-methyl)-1H-pyridin-2-one;
4-({6-[4-(4-morpholin-ylmethyl)-phenyl]-7H-pyrrolo[2,3-d]pyrimidin-4-ylamino}-methyl)-1H-pyridin-2-one;
4-({6-[4-(dimethylamino-methyl)-phenyl]-7H-pyrrolo[2,3-d]pyrimidin-4-ylamino}-methyl)-1H-pyridin-2-one;
4-({6-[4-(4-methyl-piperazin-1-ylmethyl)-phenyl]-7H-pyrrolo[2,3-d]pyrimidin-4-ylamino}-methyl)-1H-pyridin-2-one;
(2-methoxy-pyridin-4-yl)-[6-(4-morpholin-4-ylmethyl-phenyl)-7H-pyrrolo[2,3-d]pyrimidin-4-yl]-amine;
(2-methoxy-pyridin-4-yl)-{6-[4-(4-methyl-piperazin-1-ylmethyl)-phenyl]-7H-pyrrolo[2,3-d]pyrimidin-4-yl}-amine;
(2-methoxy-pyridin-4-yl)-{6-[4-(4-ethyl-piperazin-1-ylmethyl)-phenyl]-7H-pyrrolo[2,3-d]pyrimidin-4-yl}-amine;
4-{6-[4-(4-ethyl-piperazin-1-ylmethyl)-phenyl]-7H-pyrrolo[2,3-d]pyrimidin-4-ylamino}-1H-pyridin-2-one;
and pharmaceutically acceptable salts thereof.

2. A compound selected from the group consisting of
(4-methyl-piperazin-1-yl)-{4-[4-(4-fluoro-2-methyl-1H-indol-5-yloxy)-7H-pyrrolo[2,3-d]pyrimidin-6-yl]-phenyl}-methanone;
{4-[4-(4-fluoro-2-methyl-1H-indol-5-yloxy)-7H-pyrrolo[2,3-d]pyrimidin-6-yl]-phenyl}-morpholin-4-yl-methanone;
4-[4-(4-fluoro-2-methyl-1H-indol-5-yloxy)-7H-pyrrolo[2,3-d]pyrimidin-6-yl]-N,N-dimethyl-benzamide;
and pharmaceutically acceptable salts thereof.

3. A compound selected from the group consisting of
6-[4-(4-ethyl-piperazin-1-ylmethyl)-phenyl]-4-(4-fluoro-2-methyl-1H-indol-5-yloxy)-7H-pyrrolo[2,3-d]pyrimidine;
6-[4-(4-methyl-piperazin-1-ylmethyl)-phenyl]-4-(4-fluoro-2-methyl-1H-indol-5-yloxy)-7H-pyrrolo[2,3-d]pyrimidine;
4-(4-fluoro-2-methyl-1H-indol-5-yloxy)-6-(4-morpholin-4-ylmethyl-phenyl)-7H-pyrrolo[2,3-d]pyrimidine;
{4-[4-(4-fluoro-2-methyl-1H-indol-5-yloxy)-7H-pyrrolo[2,3-d]pyrimidin-6-yl]-benzyl}-dimethyl-amine;
and pharmaceutically acceptable salts thereof.

* * * * *